United States Patent [19]
Higo et al.

[11] Patent Number: 5,908,751
[45] Date of Patent: Jun. 1, 1999

[54] METHOD FOR DETECTING AND/OR DETERMINING ATP FROM MICROORGANISM CELLS IN A SAMPLE

[75] Inventors: Sachiko Higo; Reiko Tanaka, both of Tokyo, Japan

[73] Assignee: Toyo Ink Mfg. Co., Ltd., Tokyo, Japan

[21] Appl. No.: 08/845,374

[22] Filed: Apr. 24, 1997

[30] Foreign Application Priority Data

Apr. 26, 1996 [JP] Japan ..................................... 8-107444

[51] Int. Cl.$^6$ .............................. C12Q 1/68; C12Q 1/66; C12Q 1/02; G01N 33/53
[52] U.S. Cl. ..................................... 435/6; 435/8; 435/29; 435/39; 435/259; 435/267; 435/268; 435/968; 435/975
[58] Field of Search ............................... 435/6, 8, 29, 39, 435/259, 267, 268, 968, 975

[56] References Cited

U.S. PATENT DOCUMENTS

| | | | |
|---|---|---|---|
| 3,745,090 | 7/1973 | Chappelle et al. | 435/8 |
| 3,971,703 | 7/1976 | Picciolo et al. | 435/8 |
| 4,668,623 | 5/1987 | Kinnunen et al. | 435/19 |
| 5,258,285 | 11/1993 | Aegidius | 435/8 |
| 5,700,645 | 12/1997 | Pahuski et al. | 435/6 |

FOREIGN PATENT DOCUMENTS

| | | |
|---|---|---|
| 6-500462 | 1/1994 | Japan . |
| 678065 | 7/1991 | Switzerland . |
| WO 9200317 | 1/1992 | WIPO . |
| 9504276 | 2/1995 | WIPO . |

*Primary Examiner*—Leon B. Lankford, Jr.
*Assistant Examiner*—Christopher R. Tate
*Attorney, Agent, or Firm*—Pillsbury Madison & Sutro LLP

[57] ABSTRACT

The present invention provides a method for detecting and/or determining the ATP from microorganism cells in a sample, which comprises the steps of: centrifuging the sample and removing the supernatant, thereby forming a microorganism cell pellet; adding to the microorganism cell pellet a buffer containing a protease-free soluble protein and an ATP hydrolase and incubating the mixture at a pH of 6.0–8.0; extracting ATP from the microorganism cells with an added ATP extraction agent; and detecting and/or determining the ATP released from the microorganism cells by bioluminescence analysis. The present invention also provides a test kit for detecting and/or determining the ATP from microorganism cells, which comprises a reagent containing a buffer capable of pH adjustment to 6.0–8.0, a protease-free soluble protein and an ATP hydrolase, a reagent containing an ATP extraction agent, and a bioluminescence reagent.

15 Claims, 14 Drawing Sheets

METHOD FOR DETECTING AND/OR DETERMINING ATP FROM MICROORGANISM CELLS IN A SAMPLE

BACKGROUND OF THE INVENTION

The present invention relates to microbiological quality test of a sample. More specifically, the invention relates to a method for selectively detecting and/or determining the ATP from microorganism cells in a sample.

Bioluminescence analysis using luciferase is utilized as a rapid method for detecting ATP from microorganism cells. As a method for detecting the ATP from microorganism cells in a sample that is a mixture of microorganism cells and non-microorganism cells, a method is employed which comprises dissolving non-microorganism cells with a non-ionic surface active agent, decomposing the released ATP from the non-microorganism cells with an ATP hydrolase such as apyrase, inactivating the apyrase with, for example, boiling-Tris buffer, adding an agent for lysing microorganisms to the sample and quantitatively determining the ATP from the microorganism cells by bioluminescence analysis (U.S. Pat. No. 3,745,090). According to this method, test results can be obtained in only several ten minutes and, thus, this method is most appropriate for sampling inspection and the like. However, since the inactivation treatment of apyrase with boiling-Tris buffer causes a decrease in determination sensitivity, it has not been possible to obtain a correct value for the ATP level.

As a method for selectively determining the ATP from microorganism cells in a sample containing non-microorganism cells, the three methods described below have been developed (Japanese Examined Patent Publication No. 62-4120). In any of these methods, however, selective detection with a high sensitivity for the ATP from microorganism cells in the presence of the abundant ATP from non-microorganism cells is performed with much difficulty. The first method comprises treating a sample with a nonionic surface active agent to extract the ATP from non-microorganism cells, separating the ATP through a filter, extracting the concentrated ATP from microorganism cells in a filter and determining this ATP by bioluminescence analysis. This method, however, is not an appropriate method since it requires a long time and complicated operations for the filtration. The second method comprises treating a sample with a nonionic surface active agent to extract the ATP from non-microorganism cells, centrifuging the sample to remove the above ATP as a supernatant, extracting the ATP from microorganism cells from the precipitate containing microorganisms and determining this ATP by bioluminescence analysis. The drawback of this method is that the ATP from non-microorganism cells cannot be perfectly separated through one centrifugal operation. Although perfect separation is achieved by repeating centrifugal operations, these operations require a long time and are complicated. Furthermore, as the number of washing cycles (consisting of centrifugation and removal of supernatant) increases, the yield of microorganism cells decreases. Thus, this method cannot be said a good one. The third method comprises treating a sample with a nonionic surface active agent or the like to extract the ATP from non-microorganism cells, decomposing this ATP with an ATP hydrolase such as apyrase, passivating the apyrase with glass beads or the like after completion of the decomposition, then extracting the ATP from microorganism cells and determining this ATP by bioluminescence analysis. In this method, however, highly sensitive detection cannot be expected because the sample does not undergo an operation to concentrate microorganism cells and because the method is susceptible to determination inhibition by components of the sample such as proteins and milk fat. Furthermore, in this method, the removal or deactivation of the apyrase is incomplete and the inhibition action of the apyrase persists even after the extraction of ATP from microorganism cells. Thus, a correct ATP level cannot be determined. Accordingly, ATP values determined by the above three methods vary widely and, actually, the detection sensitivity that can be expected is only about $10^6$ CFU/ml (CFU: colony forming unit).

As one of the promising methods for improving detection sensitivity in bioluminescence analysis of ATP, the improvement of the above-described method including centrifugal operations in which an increase in sensitivity by concentration of microorganism can be expected may be mentioned. For milk samples, in particular, a new method has been proposed in which a chelating agent and a nonionic surface active agent are added to milk and then centrifuged in order to separate and concentrate microorganism cells from other components that inhibit the ATP determination. According to this method, determination inhibition by other milk components can be prevented. However, this method requires complicated operations, and an increase in detection sensitivity is hardly recognized since the removal of the ATP from non-microorganism cells is insufficient. Thus, as a practical testing method, insufficiency in sensitivity cannot be denied (EP-A-542790).

In view of these facts, the present invention aims at providing a method for selectively detecting and/or determining the ATP from microorganism cells in a sample at a high sensitivity and in a short time.

SUMMARY OF THE INVENTION

The present invention relates to a method for detecting and/or determining the ATP from microorganism cells in a sample, which comprises the steps of: centrifuging the sample and removing the supernatant, thereby forming a microorganism cell pellet; adding to the microorganism cell pellet a buffer containing a protease-free soluble protein and an ATP hydrolase and incubating the mixture at a pH of 6.0–8.0; extracting ATP from the microorganism cells with an added ATP extraction agent; and detecting and/or determining the ATP released from the microorganism cells by bioluminescence analysis. If the sample contains non-microorganism cells, the method may further include the step of adding a nonionic surface active agent before centrifugation of the sample such that the ATP in the non-microorganism cells is released to the outside of the cells. A chelating agent, polystyrene latex or the like may be added independently or in combination in the step of adding a nonionic surface active agent such that the ATP in the non-microorganism cells is released to the outside of the cells. Also, an ATP hydrolase-activating agent, a preservative, a chelating agent, an agent for protecting —SH groups in proteins or the like may be added independently or in combination in the step of adding to the microorganism cell pellet a buffer containing a protease-free soluble protein and an ATP hydrolase and incubating the mixture at a pH of 6.0–8.0. According to the method of the invention, it has become possible to selectively detect and/or determine the ATP from microorganism in a sample easily and in a short time. In particular, according to the method of the invention, the ATP from microorganism in a milk sample can be detected and/or determined at a detection sensitivity of $10^4$ CFU/ml or below and with a small error in determined values.

The present invention further provides a test kit for detecting and/or determining the ATP from microorganism cells, which comprises a reagent containing a buffer capable of adjusting pH to 6.0–8.0, a protease-free soluble protein and an ATP hydrolase, a reagent containing an ATP extraction agent, and a bioluminescence reagent. The test kit of the invention may further include a reagent containing a non-ionic surface active agent. The reagent containing a nonionic surface active agent may contain a chelating agent or polystyrene latex, or a combination thereof. The reagent containing a buffer capable of adjusting pH to 6.0–8.0, a protease-free soluble protein and an ATP hydrolase may contain an ATP hydrolase-activating agent, a preservative, a chelating agent or an agent for protecting —SH groups, or a combination thereof. The bioluminescence reagent may contain luciferin and luciferase.

DESCRIPTION OF PREFERRED EMBODIMENT

Figure 1:
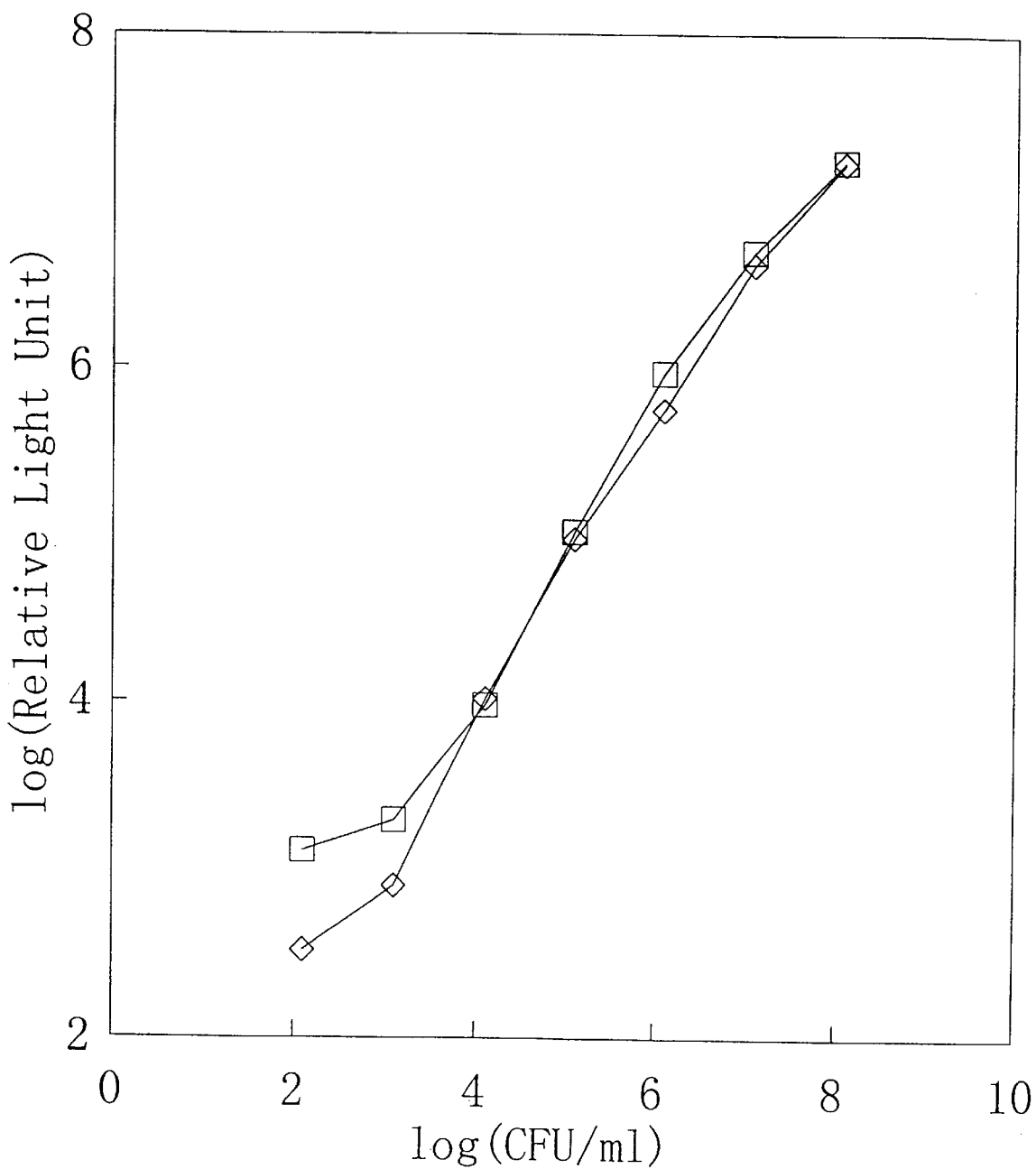
FIG. 1 shows the relation between the cell number (logCFU) and the relative light unit (logRLU) in a sample to which *Serattia liquefacience* PB 1707 has been added.
Figure 2:
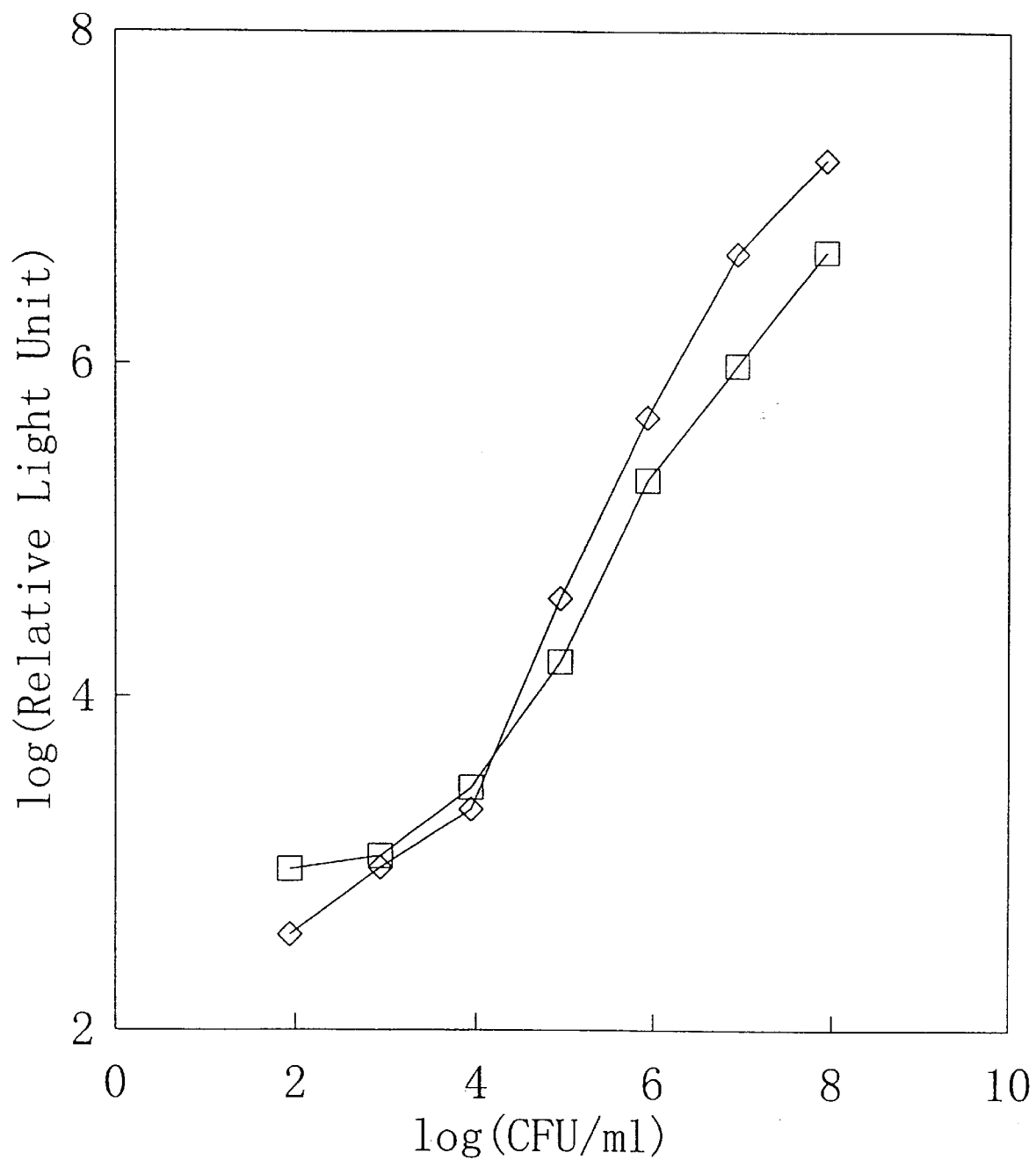
FIG. 2 shows the relation between the cell number (logCFU) and the relative light unit (logRLU) in a sample to which *Pseudomonas aeruginosa* ATCC 9027 has been added.
Figure 3:
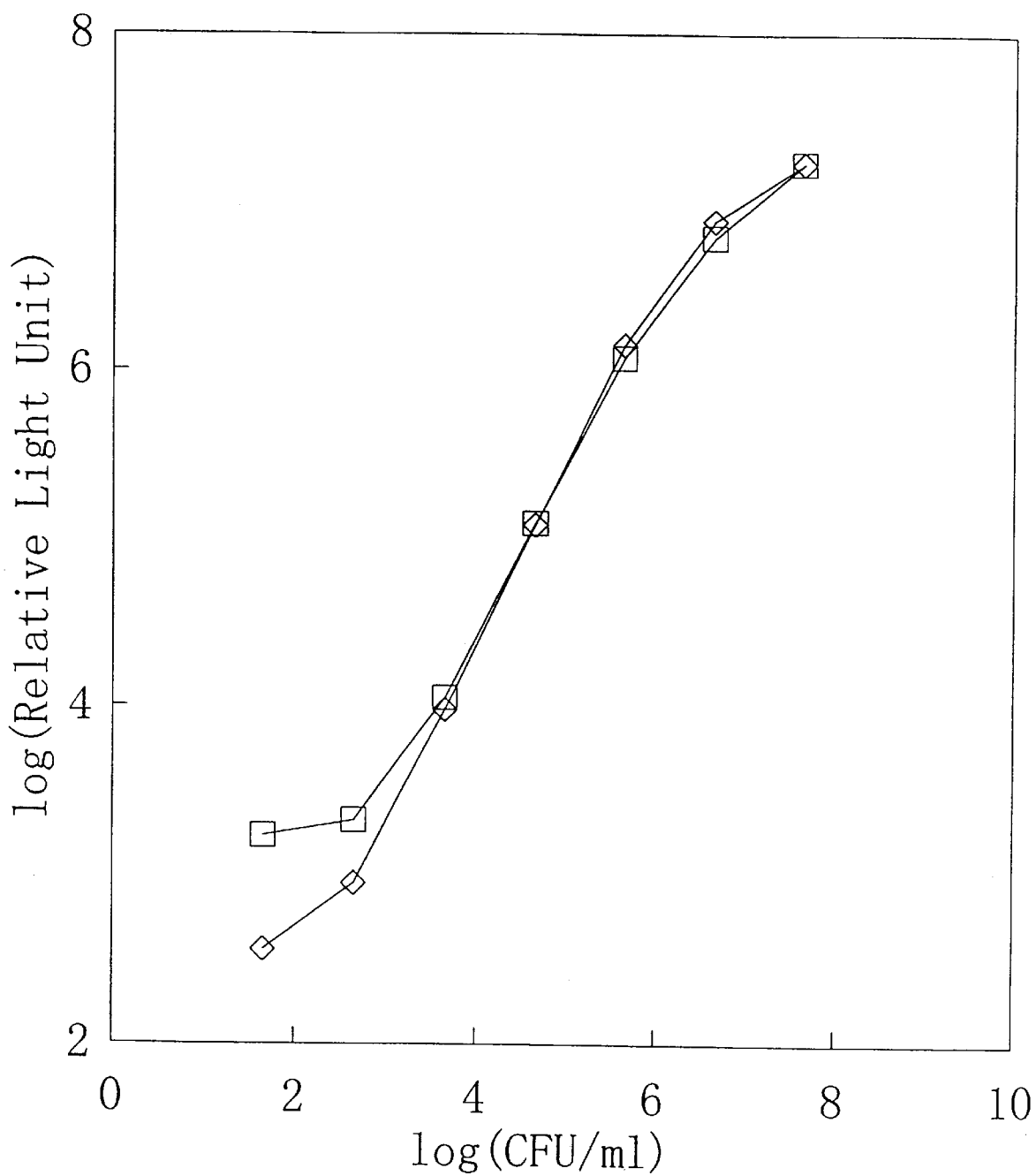
FIG. 3 shows the relation between the cell number (logCFU) and the relative light unit (logRLU) in a sample to which Enterobacter spp. has been added.
Figure 4:
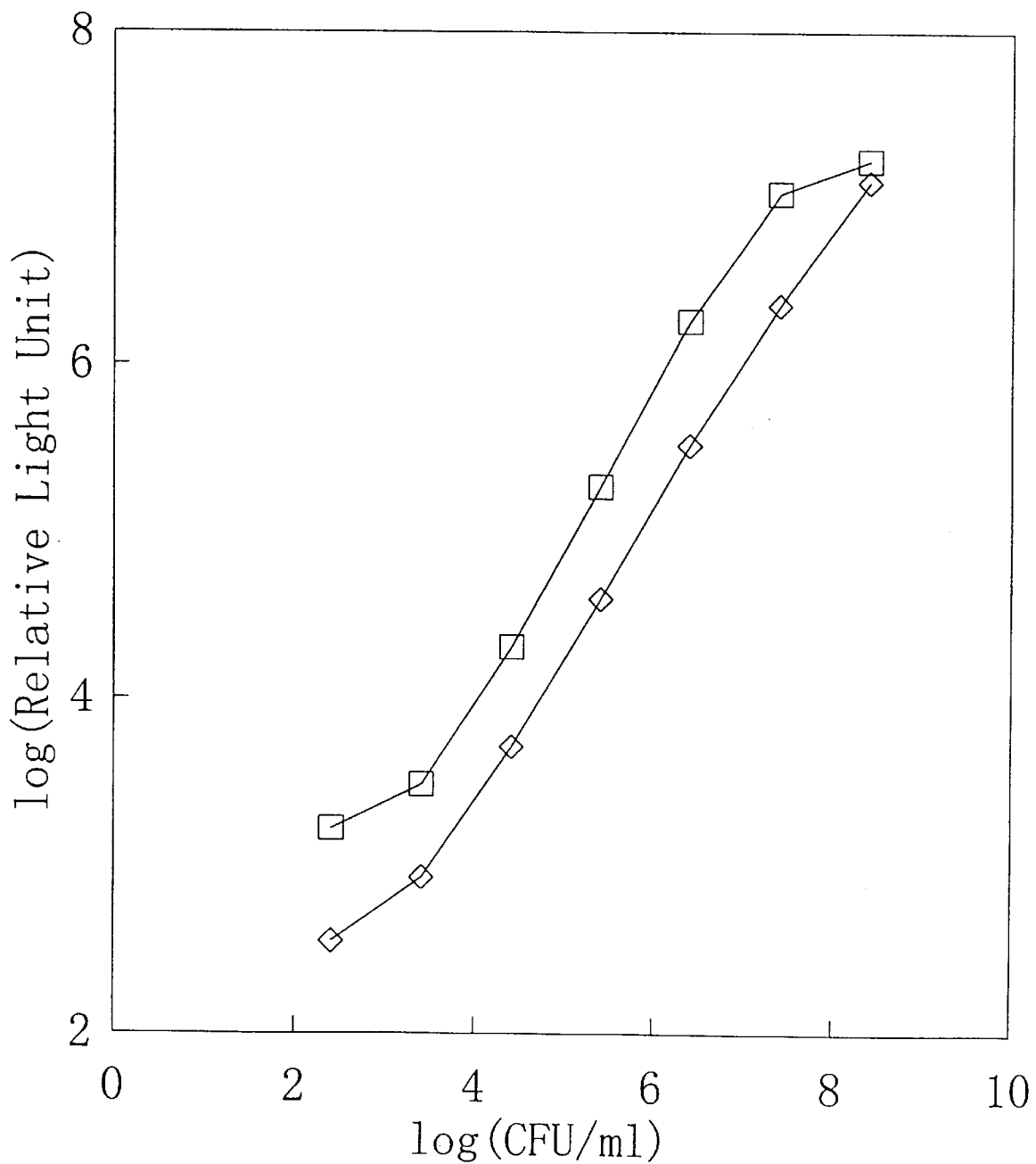
FIG. 4 shows the relation between the cell number (logCFU) and the relative light unit (logRLU) in a sample to which *Bacillus subtilis* ATCC 6633 has been added.
Figure 5:
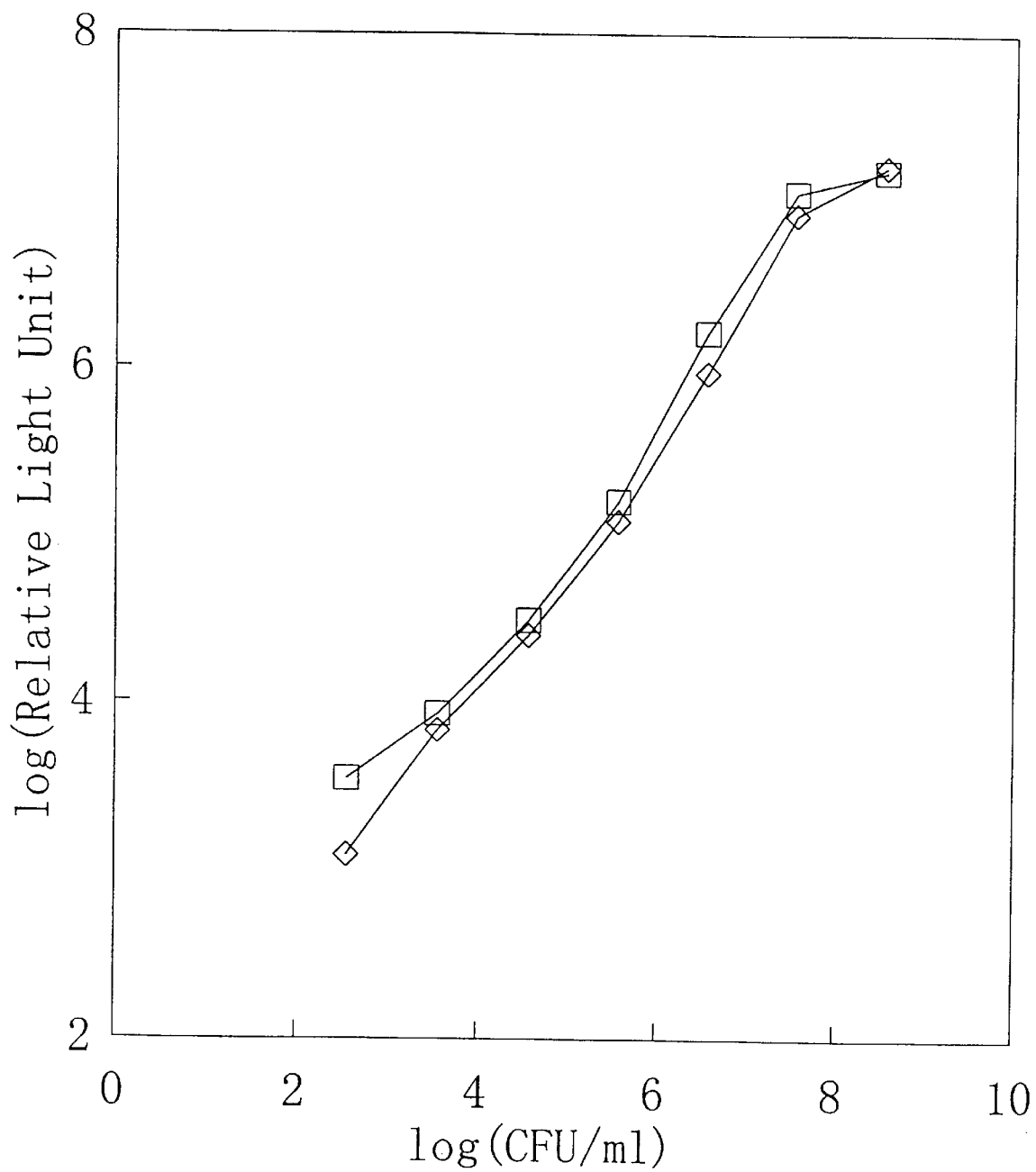
FIG. 5 shows the relation between the cell number (logCFU) and the relative light unit (logRLU) in a sample to which *Staphylococcus aureus* ATCC 6538 has been added.

Hereinbelow, the method of the present invention will be described in detail with reference to the case in which the method is applied to a milk sample that is a representative sample containing both microorganism cells and non-microorganism cells. However, this does not mean that the scope of application of the method of the invention is limited to milk samples.

First, a milk sample to be analyzed is placed in a centrifuge tube and a chelating agent and a nonionic surface active agent are added thereto. The chelating agent captures calcium ions in the milk sample to thereby inhibit the precipitation of casein, and the nonionic surface active agent serves as an agent for extracting ATP from non-microorganism cells. A lid is put on the tube containing the mixture, which is then mixed by inverting or rotating the tube. Thereafter, the sample is set in a centrifuge and centrifuged for at least 5 minutes at 10,000×g (minimum relative centrifugal force). As a result, the sample is separated into three layers. The uppermost layer consists of cream and milk protein of white or slightly yellowish white color. Below this layer is an intermediate layer forming a transparent liquid region. At the bottom is a layer of microorganism cell pellet. In order to allow the formation of a definite microorganism cell pellet, polystyrene latex or the like may be added to the milk sample together with a chelating agent and a nonionic surface active agent. The milk components other than the microorganism cell pellet are removed by suction, and only the cell pellet remains at the bottom of the centrifuge tube. The size of the microorganism cell pellet varies depending on the number of cells in the milk sample and the types of the chelating agent and nonionic surface active agent used and, the cell pellet also contains small amounts of other milk components associated with the cells.

Subsequently, a solution containing an ATP hydrolase is added to the microorganism cell pellet remaining at the bottom of the tube such that the cells are re-suspended. The re-suspension is incubated until the ATP from non-microorganism cells or the free ATP which would be the background is hydrolyzed. To the solution containing an ATP hydrolase, a buffer capable of adjusting pH to 6.0–8.0, a protease-free soluble protein and an ATP hydrolase-activating agent are added. The step of adding an ATP hydrolase is performed in order to decompose the ATP from non-microorganism cells and the free ATP. Although most of the ATP from non-microorganism cells is removed by the centrifugal operation, it is impossible to completely remove the ATP from non-microorganism cells by the centrifugal operation alone because a milk sample contains a large quantity of somatic cells. Therefore, an ATP hydrolase is added to hydrolyze these ATPs. The pH adjustment to 6.0–8.0 is performed in order to allow the ATP hydrolase to exhibit an optimum activity. The addition of a protease-free soluble protein serves to stabilize the activity of the ATP hydrolase. It is preferable to also add an ATP hydrolase-activating agent in order to stabilize the activity of the ATP hydrolase and to thereby prevent the scattering of measured values.

In the step of adding an ATP hydrolase to the microorganism cell pellet, it is convenient to control the activity and reaction conditions of the ATP hydrolase as follows:

a) The activity level of the ATP hydrolase ($\Delta$ logRLU/min) is controlled to come within a range of 1.0–4.0.

b) The reaction time of the ATP hydrolase is controlled to be 10 minutes or more.

c) The reaction temperature of the ATP hydrolase is controlled at 20–40° C.

In the present invention, the activity level of an ATP hydrolase is expressed by the rate of hydrolysis of ATP (the substrate) with the ATP hydrolase. Accordingly, determination of the enzyme activity is performed by determining the decrease in the amount of ATP in a sample over time. The amount of ATP in a sample is determined using, as an indicator, the relative light unit (RLU) obtainable from a luciferase-based bioluminescence reaction of luciferin/luciferase which is a sensitive determination method for ATP. In the present invention, a specific amount of a sample is taken in a non-continuous manner and the amount of ATP in the sample is determined by a bioluminescence reaction. From the thus obtained value, the amount of decrease in logRLU per minute ($\Delta$ logRLU/min) is calculated to thereby obtain the active level of the ATP hydrolase.

In the step of adding an ATP hydrolase to the microorganism cell pellet, the following reagents may also be added.

a) A preservative b) A chelating agent c) An agent for protecting —SH groups in proteins To the re-suspension which has undergone incubation in the presence of an ATP hydrolase, an agent for extracting ATP from microorganism cells comprising an ionic surface active agent is added such that the ATP in the microorganism cells are released. Immediately thereafter, a bioluminescence reagent (e.g., a reagent containing luciferin/luciferase) is added to induce bioluminescence from the sample and the amount of ATP is determined with a detector (e.g., a luminometer). The determination temperature at this time is preferably 15–25° C. The time period between the addition of an ATP extraction agent and the addition of a luminescence reagent is preferably from 10 to 60 seconds. The time period between the addition of a bioluminescence reagent and the completion of the determination of the light unit is preferably not more than 30 seconds.

The milk sample to be analyzed in the present invention include any liquid solutions derived from milk products. Specific examples include raw milk, raw goat's milk, raw sheep's milk, cow's milk, ultra-high temperature pasteurized milk, low temperature long term pasteurized milk, pasteurized goat's milk, special milk, partially defatted milk, defatted milk, processed milk, milk powder reconstituted with water, cream, skim milk, liquefied ice cream, ice milk or related products, soybean milk, milk in the sample, a raw material for milk containing a suspension, a mixed solution with coffee or the like, culture solution comprising milk (enrichment culture solution).

The term "microorganism(s)" used herein means unicellular prokaryotes. Specific examples include bacteria or non-eukaryotes. Eukaryotes are those organisms in which genetic materials are enclosed in a nucleus.

The term "non-microorganism cells" used herein refers to cells which are not microorganisms. Most of them are somatic cells which comprise all of the cells constituting an organism except reproductive cells. Somatic cells include, for example, cells such as leukocytes, erythrocytes, platelets and the like from body fluid; and cells abraded from internal mammary tissues, muscular tissues, dermal tissues and the like.

ATP (adenosine-5'-triphosphate) is a nucleotide made of adenine, D-ribose and 3 phosphate groups, and is generated by phosphorylation reaction in breathing, fermentation and photosynthesis. ATP is important in biological energy metabolism. Every living cell contains ATP.

The chelating agent used in the invention include any molecule or macromolecule which binds to a divalent metal ion such as the calcium ion, magnesium ion, iron ion, cadmium ion, beryllium ion, cobalt ion, nickel ion, cupper ion, lead ion; or other metal ions. This molecule may be a synthetic or natural organic compound; a protein, carbohydrate or lipid capable of binding to the above ions; a copy or modified product of an organism derived-molecule; or the like.

If a chelating agent is added to a milk sample before the centrifugal operation, casein micelles in the milk sample are dissociated into submicelles due to the action of the chelating agent (L. C. Chaplin, J. Dairy Res., 51, 251–257 (1984)). If the milk sample is subjected to similar centrifugal operation without the addition of a chelating agent, the supernatant of the milk sample is not clarified and micelle-like milk protein is suspending in the centrifuge tube or casein micelles which have obtained a large molecular weight through association precipitate and form a large pellet at the bottom of the tube. Thus, a definite microorganism cell pellet is not formed. A chelating agent binds to calcium ions which is a major component contributing to the micelle structure to thereby dissociate casein micelles. Accordingly, a chelating agent which binds to calcium ions is preferable in the present invention.

As this chelating agent, ethylenediaminetetraacetic acid (EDTA; product name: Versene), bis-(O-aminophenoxy)-ethane-N,N,N',N'-tetraacetic acid (BAPTA), ethylene glycol-bis-($\beta$-aminoethyl ether) N,N,N',N'-tetraacetic acid (EGTA), nitrilotriacetic acid (triglycine, ammoniatriacetic acid, Trilon A), trans-1,2-diaminocyclohexanetetraacetic acid (CDTA), diethylenetriaminopentaacetic acid (DTPA), N-(2-acetamide)iminodiacetic acid (ADA), citrate, arginine, hypoxanthine, 4, 5-dihydroxybenzene-1,3-disulfonic acid, a crown ether type compound, or any derivative or precursor of these molecules may be used.

It is very important for the chelating agent to be used in the present invention that it should not act upon the cells to be detected. In addition, a chelating agent which does not affect bioluminescence analysis (e.g., analysis using luciferin/luciferase) is preferable. Those chelating agents which are found especially excellent for use in the invention are nitrilotriacetic acid, ethylenediaminetetraacetic acid and N-(2-acetamide)iminodiacetic acid.

The nonionic surface active agent to be used in the invention is a surface active agent which does not have a group that dissociates into ions in aqueous solution and which acts as an agent for extracting ATP from non-microorganism cells. In order to separate and remove non-microorganism cells from the milk sample and to separate and concentrate only microorganism cells, especially it is preferable to use an agent which extracts ATP from non-microorganism cells without affecting microorganism cells. Therefore, an agent is desired which has a gentle denaturing action upon proteins and which is excellent in the ability to solubilize membranes and which contributes to the emulsification and dispersion of aggregating milk components to thereby further facilitate the separation/concentration of microorganisms.

Nonionic surface active agents are roughly classified into three groups; 1) those which are obtained by linking ethylene glycol to higher alcohols, alkyl phenols, fatty acids and the like as a hydrophilic group, 2) partial esters of polyvalent alcohols, monoglycerides which are higher fatty acid glycerol esters, and fatty acid esters of sorbitol, 3) addition polymers from polypropylene glycol and polyethylene glycol may be enumerated. Among the nonionic surface active agents described above, Triton X-100 (octyl phenoxy polyethoxyethanol) or Nonidet P-40 (NP-40) (both of which are polyoxyethylene glycol octylphenyl ethers) is preferable. Especially, Triton X-100 is preferable. Among all, it is especially preferred that such a nonionic surface active agent be added to a milk sample together with a chelating agent. Most of somatic cells are lysed by the treatment prior to the centrifugation. After the centrifugation, the influence of the ATP from non-microorganism cells is reduced. The amount of addition of a nonionic surface active agent is 0.1–5%, preferably 0.25–2.5% relative to the milk sample when Triton X-100 is used. In the preparation of a test kit for milk samples, the chelating agent described previously and the above nonionic surface active agent may be provided in the form of a solution dissolving both agents.

The term "microorganism cell pellet" used herein refers to a material formed separately at the bottom of a centrifuge tube mainly by microorganism cells which have precipitated on centrifugation. The size of a microorganism cell pellet depends on the number of microorganism cells contained in the milk sample and the types of the chelating agent and/or the nonionic surface active agent used. A microorganism cell pellet may contain small amounts of other milk components associated with microorganism cells. Usually, a microorganism cell pellet obtainable from 1.0 ml of a milk sample is 10–40 µl. The external appearance of a microorganism cell pellet is white or slightly grayish white.

If the number of microorganism cells in the milk sample is small, a microorganism cell pellet formed on centrifugation is small and there is the possibility that it might erroneously be removed by suction operation. Accordingly, in order to allow the formation of a definite microorganism cell pellet, polystyrene latex or the like may be added to the milk sample together with a chelating agent and a nonionic surface active agent. Also, in the preparation of a test kit for milk samples, polystyrene latex or the like may be added to a solution containing a chelating agent and a nonionic surface active agent.

The ATP hydrolase used in the invention is an ATP hydrolase which cuts off the terminal phosphate group of ATP to generate ADP or AMP and inorganic phosphate. Specific examples include apyrase which is extracted and purified mainly from potato and ATP pyrophosphatase. Preferably, apyrase is used since it is easily available as a commercial product.

The ATP hydrolase is used as a means to decompose the ATP from non-microorganism cells in the sample and thereby to detect the ATP from microorganism cells at a higher sensitivity. By adding to the milk sample a solution containing a chelating agent and a nonionic surface active agent and then centrifuging the sample, a microorganism cell pellet is separated and microorganism cells are concentrated. However, non-microorganism cells such as somatic cells are present abundantly in the initial sample, and the ATP from the non-microorganism cells which has not been removed by centrifugation remains in the sample in a large quantity. By adding a solution containing an ATP hydrolase, it becomes possible to remove completely the ATP from the non-microorganism cells which would otherwise be the background. Therefore, if an ATP hydrolase is to be used, it is desirable to select one having an activity capable of quickly decomposing the ATP from non-microorganism cells and to ensure that the ATP hydrolase remaining after use will have a minimun influence on the ATP from microorganism cells to be detected subsequently.

In the step of adding an ATP hydrolase to a microorganism cell pellet, pH is adjusted to 6.0–8.0, preferably 6.5–7.8 at which an ATP hydrolase acts in a most stable manner. In the adjustment of pH, those buffers exhibiting a neutral pH value described on pages 432–435 in *Basic Experimental Methods on Proteins and Enzymes* (authored and edited by Horio and Yamashita, published by Nanko-do, Co. (1981)) may be used. Among those buffers, the buffers generically known as Good's buffer, e.g., MES (2-morpholinoethanesulfonic acid) buffer, Tris (tris (hydroxymethyl)aminomethane) type buffer, BES (N,N-bis (2-hydroxyethyl)-2-aminoethanesulfonic acid) buffer, MOPS (3-morpholinopropanesulfonic acid) buffer, HEPES (N-2-hydroxyethylpipera zine-N-2-ethanesulfonic acid) buffer and the like are preferably used.

In the step of adding an ATP hydrolase to the microorganism cell pellet, a protease-free soluble protein is added for the purpose of activating and stabilizing the ATP hydrolase. As the soluble protein to be added, any protein derived from animals, plants or microorganisms may be used as long as the protein does not exhibit the proteolytic activity recognized in such proteins as papain, trypsin, chymotrypsin, etc. Preferably, one or more proteins selected from ovalbumin, lactoalbumin, serum albumin, leucosin, legumerin and ricin which are soluble proteins generically called albumin are used. A protease-free soluble protein is added in an amount of 0.10–5 mg, preferably 0.25–2.5 mg per 1 ml of milk sample.

Additionally, in the step of adding an ATP hydrolase to a microorganism cell pellet, calcium ion, magnesium ion and the like may also be added as an ATP hydrolase-activating agent. Calcium ion is added in an amount of 0.1–50 mM, preferably 1–20 mM, per 1 ml of milk sample, and magnesium ion is added in an amount of $1/100$–$1/10$ of that of calcium ion.

In the above-described step of adding an ATP hydrolase, the ATP hydrolysis activity level ($\Delta$ logRLU/min) is preferably 1.0–4.0, more preferably 2.0–3.0; the reaction temperature is preferably 20–40° C., more preferably 25–35° C.; and the reaction time is preferably 10 minutes or more, more preferably 10–30 minutes.

Under these conditions, the ATP from non-microorganism cells which would otherwise be the background is sufficiently decomposed, and hydrolysis of the ATP from microorganism cells does not proceed in a short period of time during the bioluminescence by a luminescence reagent containing luciferin/luciferase. Therefore, the present invention is characterized in that a treatment/operation to deactivate the ATP hydrolase is unnecessary. Also, the repetition of centrifugal operations which is practiced conventionally is not necessary. According to the method of the invention, the operation for determining the number of microorganism cells in a microorganism cell pellet can be remarkably simplified. Also, under the conditions described above, the decomposition of the ATP from non-microorganism cells which would be the background for the determination proceeds sufficiently and, thus, lowering and stabilization of the background value have become possible. Accordingly, the detection sensitivity for the ATP from microorganism cells can be remarkably improved. In the present invention, an ATP hydrolase, a protease-free soluble protein, an ATP hydrolase-activating agent and a buffer for pH adjustment may be mixed and added as one solution.

In the step of adding an ATP hydrolase to a microorganism cell pellet, the addition of a preservative, chelating agent and agent for protecting —SH groups in proteins may also be effective. A preservative is added for the purpose of minimizing the influence of microorganisms which may contaminate the sample during the determination. Specific examples include antibiotics such as a sodium salt of penicillin G, a potassium salt of penicillin G, ampicillin, chloramphenicol, streptomycin, kanamycin, tetracycline, oxytetracycline; azides such as sodium azide; phenol compounds such as cresol; and acids such as lactic acid, citric acid, benzoic acid, propionic acid, dehydroacetic acid, oxybenzoic acid, sorbic acid.

The chelating agent to be added in this step is different in purpose from the one used in the step of adding a nonionic surface active agent such that the ATP in non-microorganism cells are released to the outside of the cells. Here, the chelating agent is used mainly as an agent for capturing heavy metals. However, those agents described previously, i.e., ethylenediaminetetraacetic acid (EDTA; product name: Versene), bis-(O-aminophenoxy)-ethane-N,N,N',N'-tetraacetic acid (BAPTA), ethylene glycol-bis-(β-aminoethyl ether) N,N,N',N'-tetraacetic acid (EGTA), nitrilotriacetic acid (triglycine, ammoniatriacetic acid, Trilon A), trans-1,2-diaminocyclohexanetetraacetic acid (CDTA), diethylenetriaminopentaacetic acid (DTPA), N-(2-acetamide)iminodiacetic acid (ADA), citrate, arginine, hypoxanthine, 4, 5-dihydroxybenzene-1,3-disulfonic acid, a crown ether type compound, and any derivative or precursor of these molecules may be used. Among all, EDTA is especially preferable since this agent does not act on the cells to be detected nor affect the bioluminescence analysis.

An agent for protecting —SH groups in proteins is added in order for an ATP hydrolase to act stably. As this agent, glutathione, dithiothreitol (DTT), mercaptoethanol, cysteine or dithioerythritol may be used. DTT is especially preferable.

In the step of adding an ATP hydrolase to the microorganism cell pellet, saccharides such as glucose, fructose, arabinose, xylose, saccharose, trehalose, lactose, maltose, xylobiose; sugar alcohols such as mannitol, xylitol, dulcitol, sorbitol, ribitol, glucitol; water-soluble polymers such as PEG (polyethylene glycol) #400, PEG #600; amino acids such as glycine, serine, proline, glutamic acid, alanine; amines such as trimethylamine; and polyvalent alcohols such as glycerol may also be added in order to maintain the activity of the ATP hydrolase.

The ATP extraction agent to be used in the invention is an agent that is used to act upon the separated and concentrated microorganism cells from the milk sample so that the ATP in the microorganism cells are released to the outside of the cells. This agent is a lysis agent which alters or disrupts the structure of microorganism cells, and includes any cellular membrane-solubilizing agent, either natural or synthetic, such as surface active agents, acids, alkalis, enzymes, salts, chelating agents and organic solvents.

As the ATP extraction agent used in the invention, an ATP extraction agent which is mild in denaturing action upon luciferase and excellent in the ability to solubilize membranes and which does not give a remarkable influence upon the detection of luminescence is preferable. Specific examples of agents which may be used as an ATP extraction agent include quaternary ammonium salts such as cetyltrimethylammonium bromide (CTAB), dodecyltrimethylammonium bromide, cetylpyridinium chloride, benzalkonium chloride, benzethonium chloride; cationic surface active agents such as chlorhexidine digluconate; anionic surface active agents such as sodium dodecyl sulfate; and nonionic surface active agents such as Triton X-100, Nonidet P-40 (NP-40). Among all, quaternary ammonium salts and chlorhexidine digluconate are preferable since they are quick in extraction and inhibit the luciferase reaction less.

The ATP released from microorganisms is determined by bioluminescence analysis. In the present invention, a previously described method for quantitatively determining ATP with luciferase (M. A. DeLuca, Advances in Enzymology, 44, 37–68 (1976)) can be applied to quantitative determination of the number of microorganism cells in the milk sample. This ATP determination method may be applied to quantitative determination of the number of either eucaryotic or procaryotic cells. The number of microorganism cells present in the sample is calculated based on the relation between the amount of ATP in the sample determined and the average amount of ATP present in a microorganism cell.

Luciferase used as a means to detect ATP is unstable to temperature. Therefore, the room temperature at the time of determination is reflected in the amount of luminescence (i.e., determined value) and, thus, determined values vary even if the amount of ATP is the same. In other words, when the same amount of ATP is determined, the amount of luminescence is maximum at around 20° C. and the amount decreases above or below 20° C. Therefore, in order to maximize the detection sensitivity, to reduce the dispersion in determination results and to increase the reliability, the luciferase reaction temperature and the room temperature at the time of determination should be controlled at 30° C. or below, preferably at 15–25° C.

Since deactivation of the ATP hydrolase is not performed in the present invention, the ATP from microorganism cells is gradually decomposed after the addition of the ATP hydrolase. Therefore, the time which may be spent from the addition of an ATP extraction agent to the addition of a bioluminescence reagent comprising luciferin/luciferase is appropriately from 10 seconds to 60 seconds. Especially preferable is 10 seconds or less. Similarly, the time from the addition of a bioluminescence reagent to the determination of the amount of luminescence is preferably 20 seconds or less. Especially preferable is 10 seconds or less.

In the method of the invention, the ATP from those non-microorganism cells mixed in a cell pellet can be completely decomposed by adding a sufficient amount of a nonionic surface active agent to a sample, thereby extracting the ATP from non-microorganism cells completely, separating and removing the ATP as a supernatant, and then adding an ATP hydrolase to the cell pellet. In milk samples in particular, non-microorganism cells such as somatic cells are present abundantly and the removal of them is very important. The unfavorable detection sensitivity in conventional methods is attributable to the fact that those methods have tried to separate or decompose the ATP from non-microorganism cells by a single operation of centrifugation or addition of an ATP hydrolase. In the present invention, the ATP from non-microorganism cells is not only separated by centrifugation but also decomposed by an ATP hydrolase by finding out optimumal conditions under which ATP hydrolases function effectively. Thus, the invention has enabled selective, highly sensitive detection of microorganism cells.

In the step of adding an ATP hydrolase, the activity level of this hydrolase is optimized by adjusting the pH to 6.0–8.0 with a buffer and by adding a protease-free soluble protein. An ATP hydrolase functions well when decomposing the ATP from non-microorganism cells, but its action becomes slow when the ATP from microorganism cells has been extracted with an ionic surface active agent. Thus, the amount of the ATP from microorganism cells can be selectively detected if determined quickly by bioluminescence analysis. Particularly, by strictly limiting the conditions under which an ATP hydrolase is to be used, it is possible to decompose the ATP from non-microorganism cells remaining in a cell pellet and, at the same time, to minimize the decomposition of the ATP from microorganism cells. Furthermore, it was effective for the selective detection of the ATP from microorganism cells to shorten not only the time required for ATP extraction from microorganism cells after the decomposition treatment of the ATP from non-microorganism cells with an ATP hydrolase but also the time required for the treatment with a bioluminescence reagent comprising luciferin/luciferase. By combining a series of the above-described operations, detection sensitivity could be improved; scattering of determined values could be reduced and their reliability could be increased.

The method of the invention has been described so far taking a milk sample as an example. However, the method of the invention is also applicable to other samples such as raw meat, raw vegetables, fishes and shells, processed food, drinks (e.g., beer, juice), potable water, industrial water (e.g., white water in the paper manufacturing industry, dampening water in the printing industry), and the like. In the case of detecting and/or determining the ATP from microorganism cells in a sample of, for example, a drink, potable water or industrial water, the step of adding a nonionic surface active agent such that the ATP in non-microorganism cells in the sample is released to the outside of the cells may be omitted.

The present invention further includes a test kit for detecting and/or determining the ATP from microorganism cells, which comprises a reagent containing a buffer capable of adjusting pH to 6.0–8.0, a protease-free soluble protein and an ATP hydrolase, a reagent containing an ATP extraction agent, and a bioluminescence reagent. This test kit may further include a reagent containing a nonionic surface active agent. The reagent containing a buffer capable of adjusting pH to 6.0–8.0, a protease-free soluble protein and an ATP hydrolase may contain an ATP hydrolase-activating agent, preservative, chelating agent, agent for protecting —SH groups, sugar, polyvalent alcohol, water-soluble polymer, amino acid, amines, organic solvent or the like in addition to the buffer, protein and hydrolase as described above. This reagent may be powdered by freeze-drying or the like. The thus powdered reagent may be dissolved in a buffer containing a preservative such as sodium azide, a chelating agent and the like (e.g., Good's buffer such as HEPES buffer and MOPS buffer). The reagent containing an ATP extraction agent contains the nonioic surface active agent described above. This reagent may also contain an acid such as trichloroacetic acid, alkali, enzyme such as lysozyme, chelating agent, organic solvent and the like. The bioluminescence reagent may be any reagent as long as it allows for ATP detection by bioluminescence. For example, this reagent contains an enzyme (luciferase) and its substrate (luciferin) for a bioluminescence reaction. Specific examples include those enzymes and substrates derived from fireflies, luminous click beetles, insects of family Omethidae and the like. The bioluminescence reagent may also contain a buffer, chelating agent, divalent cation such as magnesium or calcium, agent for protecting —SH groups in proteins, protease-free soluble protein, preservative, polyvalent alcohol, water-soluble polymer, amino acid, amines, organic solvent and the like.

When using of this test kit, individual reagents may be mixed before use. Alternatively, an individual reagent may be mixed immediately before the start of the relevant step.

The test kit of the invention may take the form of storage means which is partitioned so that one or more containers such as vials and tubes containing respective reagents are placed together in one compartment. Preferably, each reagent is sterilized before being packed in a container. Furthermore, each of the solution-type reagents containing an enzyme may be powdered by dehydration by means of freeze-drying or the like and tightly sealed to improve the keeping quality. Preferably, a tightly sealed container is either in vacuo and/or filled with nitrogen gas so that no oxygen is present in the container. When a reagent has been thus powdered by means of freeze-drying or the like, it is preferable to dissolve the reagent in sterilized water or a buffer immediately before use and to use the resuspended solution.

Hereinbelow, the present invention will be described with reference to the following Examples, which should not construed as limiting the scope of the present invention.

EXAMPLE 1

1) The following five microorganisms shake cultured overnight at 30° C. in 5 ml of nutrient broth (NB) liquid medium individually are subjected to serial 10-fold dilutions in sterilized water.

*Serattia liquefacience* PB 1707
*Pseudomonas aeruginosa* ATCC 9027
Enterobacter spp.
Bacillus subtilisATCC 6633
*Staphylococcus aureus* ATCC 6538

2) To a 1.5 ml centrifuge tube with a cap, 1 ml of the following milk sample is added.

A milk sample: commercial ultra high temperature pasteurized milk

3) A 10 µl aliquot is taken from each of the dilutions prepared in 1) above, inoculated into the milk sample of 2) above contained in the centrifuge tube, and left at room temperature for about 10 minutes.

4) To the centrifuge tube, 500 µl of an aqueous solution containing the following chelating agent and nonionic surface active agent is added, and then the tube is capped.

Composition of the aqueous solution containing a chelating agent and nonionic surface active agent:

| Polystyrene latex | 0.01% |
|---|---|
| Triton X-100 | 0.5% |
| EDTA | 0.15M |

5) After mixing, the mixture is centrifuged at 12,000×g for 5 minutes to thereby separate a microorganism cell pellet from other milk components.

6) From the separated microorganism cell pellet, milk components other than the pellet are removed by suction with an aspirator.

7) To the microorganism cell pellet remaining at the bottom of the centrifuge tube, 100 µl of the following aqueous solution containing an ATP hydrolase is added and agitated to thereby suspend the microorganism cells. Then, the suspension is incubated at 25° C. for 30 minutes to decompose the non-microorganism ATP.

Composition of the aqueous solution containing an ATP hydrolase Apyrase (from potato; Sigma; Grade VI)
Enzyme activity (Δ logRLU/min.)=2.0

| Ovalbumin (from hen's egg; Sigma; Grade VI) | 1 mg/ml |
|---|---|
| $CaCl_2$ | 2 mM |
| $MgCl_2$ | 0.05 mM |
| Penicillin G-Na salt (Sigma) | 0.1% |
| EDTA | 0.1 mM |

-continued

| | |
|---|---|
| DTT | 1 mM |
| MOPS/NaOH buffer (pH 7.0) | 25 mM |

8) After completion of the reaction, the suspension is transferred to a measurement cell, to which 100 µl of an ATP extraction agent is added and reacted for 10 seconds such that ATP is released from microorganism cells.

Composition of the ATP extraction agent:

| | |
|---|---|
| CTAB | 0.0075% |

9) To the reaction solution containing the ATP released from the microorganism cells, 100 µl of a luminescence agent containing luciferin/luciferase (Toyo Ink Mfg. Co., Ltd.; product name: Kinshiro) is added and an integrated value of luminescence for 10 seconds after the addition of the luminescence agent is determined. Thus, the relative light unit (logRLU) of sample A which is an artificially contaminated milk is obtained.

10) On the other hand, sample B is prepared as a positive control in the following manner. Ten µl of each of the diluents prepared in 1) above (i.e., microorganism cells equal in number to those contained in sample A) is placed in a measurement cell of a luminometer, to which 100 µl of an ATP extraction agent is added and lysed for 10 seconds. Thereafter, the luminescence agent (Toyo Ink Mfg. Co., Ltd.; product name: Kinshiro) is added and an integrated value of luminescence for 10 seconds after the addition of the luminescence agent is determined. Thus, the relative light unit (logRLU) of sample B is obtained.

11) The number of microorganism cells in sample A and the number in sample B are equal. Hence, 100 µl of each of the dilutions prepared in 1) above is spread on a standard agar medium and cultured at 30° C. for 48 hours. The number of colonies grown on the medium is counted and the number of cells contained in 10 µl of each dilution is calculated, to thereby obtain the cell numbers (logCFU) for samples A and B.

FIGS. 1, 2, 3, 4 and 5 show the relation between the cell number (logCFU) and the relative light unit (logRLU) for each of the microorganisms. In both sample A (□) and sample B (◊), linearity is observed between the cell number and the relative light unit when the cell number (logCFU) is in the range of from 3 to 8. Thus, it is possible to quantitatively determine the cell number (logCFU) from the relative light unit (logRLU). Also, good correlation is observed between the relative light unit (logRLU) and cell number (logCFU) of sample A (which is an artificially contaminated milk) and those of sample B (which is milk-free). It is shown that only the ATP from microorganism cells can be determined with little damage from milk which is a typical sample containing both microorganism cells and non-microorganism cells. Also, it is shown that the cell number (logCFU) can be quantitatively determined from the relative light unit when the cell number (logCFU) is in the range of from 3 to 8.

EXAMPLE 2

The following Examples 2–7 show the results of experiments using *Staphylococcus aureus* ATCC 6538, a representative microorganism which contaminates milk samples.

Figure 6:
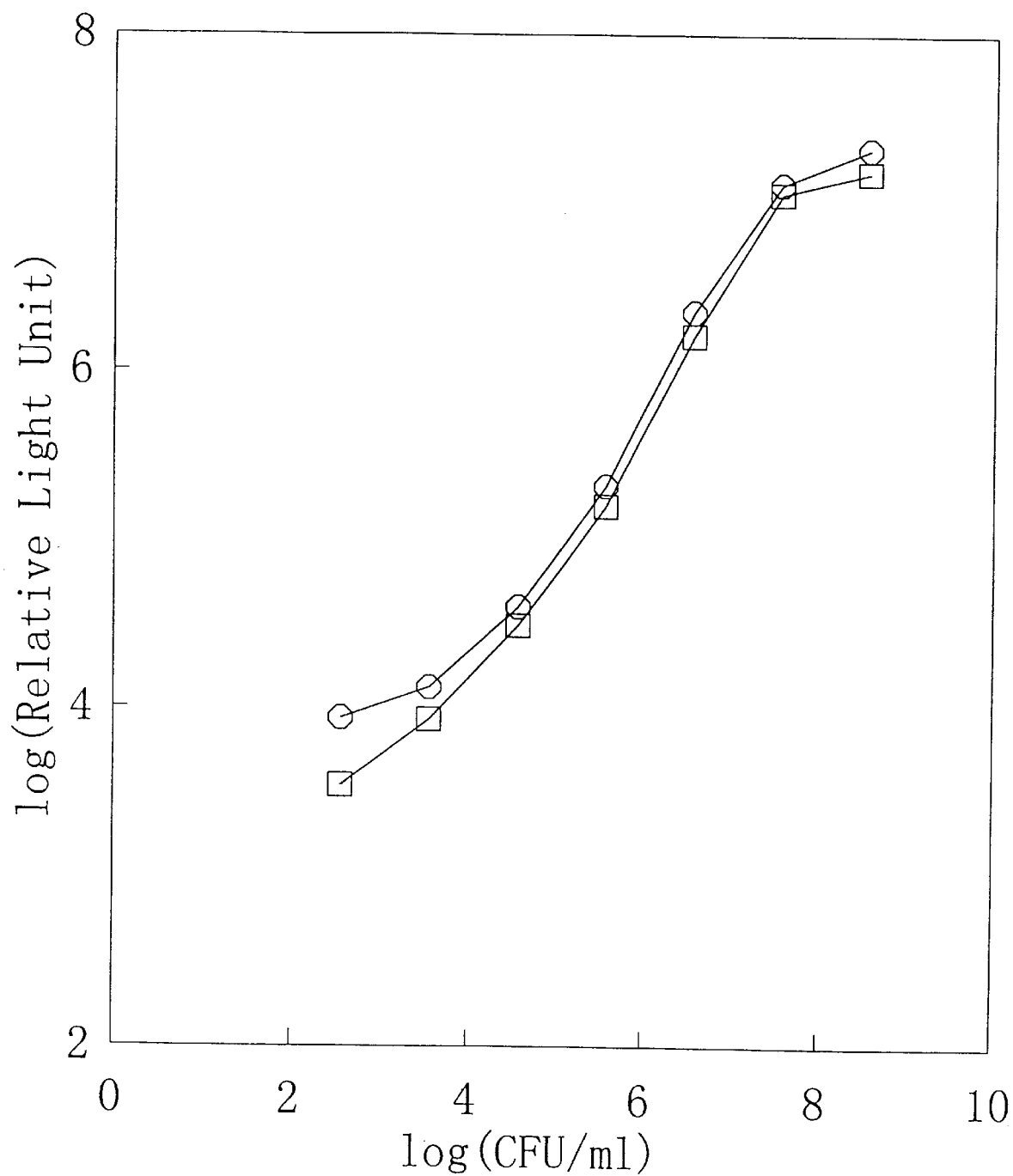
FIG. 6 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that serum albumin (from bovine; INTERGEN) was used instead of ovalbumin as a protease-free soluble protein at the same concentration in the ATP hydrolase-containing aqueous solution shown in step 7) of Example 1. The results are shown in FIG. 6. In this Figure, ○ represents the results of Example 2 and □ represents the results for sample A in Example 1.

When bovine serum albumin is used, linearity is also observed between the cell number and the relative light unit if the cell number (logCFU) is in the range of from 3 to 8. Also, good correlation is observed with sample A of Example 1. Thus, it is shown that the cell number (logCFU) can be quantitatively determined from the relative light unit when the cell number (logCFU) is in the range of from 3 to 8.

EXAMPLE 3

Figure 7:
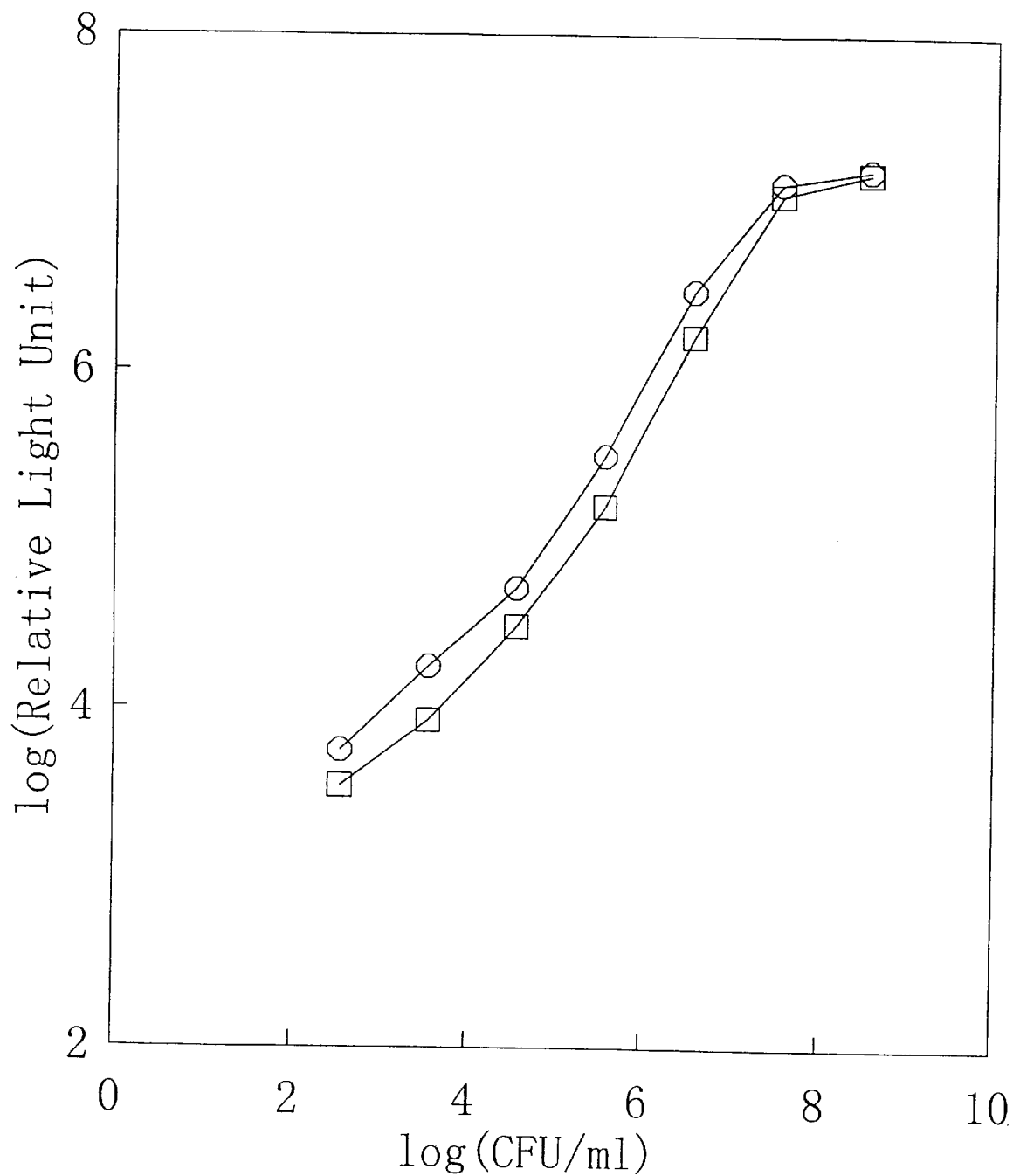
FIG. 7 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that serum albumin (from pig; Sigma) was used instead of ovalbumin as a protease-free soluble protein at the same concentration in the ATP hydrolase-containing aqueous solution shown in step 7) of Example 1. The results are shown in FIG. 7. In this Figure, ○ represents the results of Example 3 and □ represents the results for sample A in Example 1.

When pig serum albumin is used, linearity is also observed between the cell number and the relative light unit when the cell number (logCFU) is in the range of from 3 to 8. Also, good correlation is observed with sample A of Example 1. Thus, it is shown that the cell number (logCFU) can be quantitatively determined from the relative light unit when the cell number (logCFU) is in the range of from 3 to 8.

EXAMPLE 4

Figure 8:
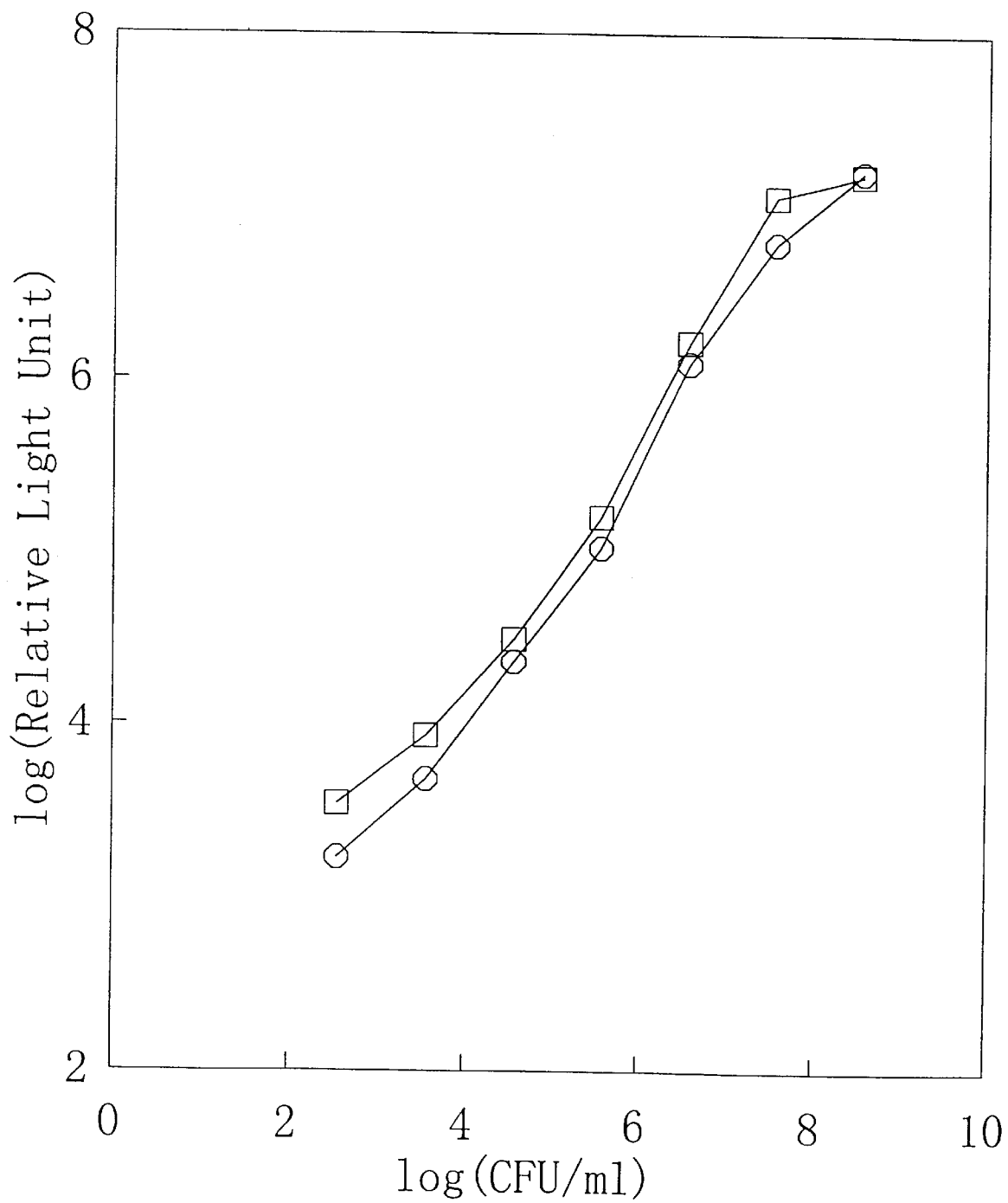
FIG. 8 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that lactoferrin (from cow's milk; Sigma) was used instead of ovalbumin as a protease-free soluble protein at the same concentration in the ATP hydrolase-containing aqueous solution shown in step 7) of Example 1. The results are shown in FIG. 8. In this Figure, ○ represents the results of Example 4 and □ represents the results for sample A in Example 1.

When lactoferrin is used, linearity is also observed between the cell number and the relative light unit if the cell number (logCFU) is in the range of from 3 to 8. Also, good correlation is observed with sample A of Example 1. Thus, it is shown that the cell number (logCFU) can be quantitatively determined from the relative light unit when the cell number (logCFU) is in the range of from 3 to 8.

EXAMPLE 5

Figure 9:
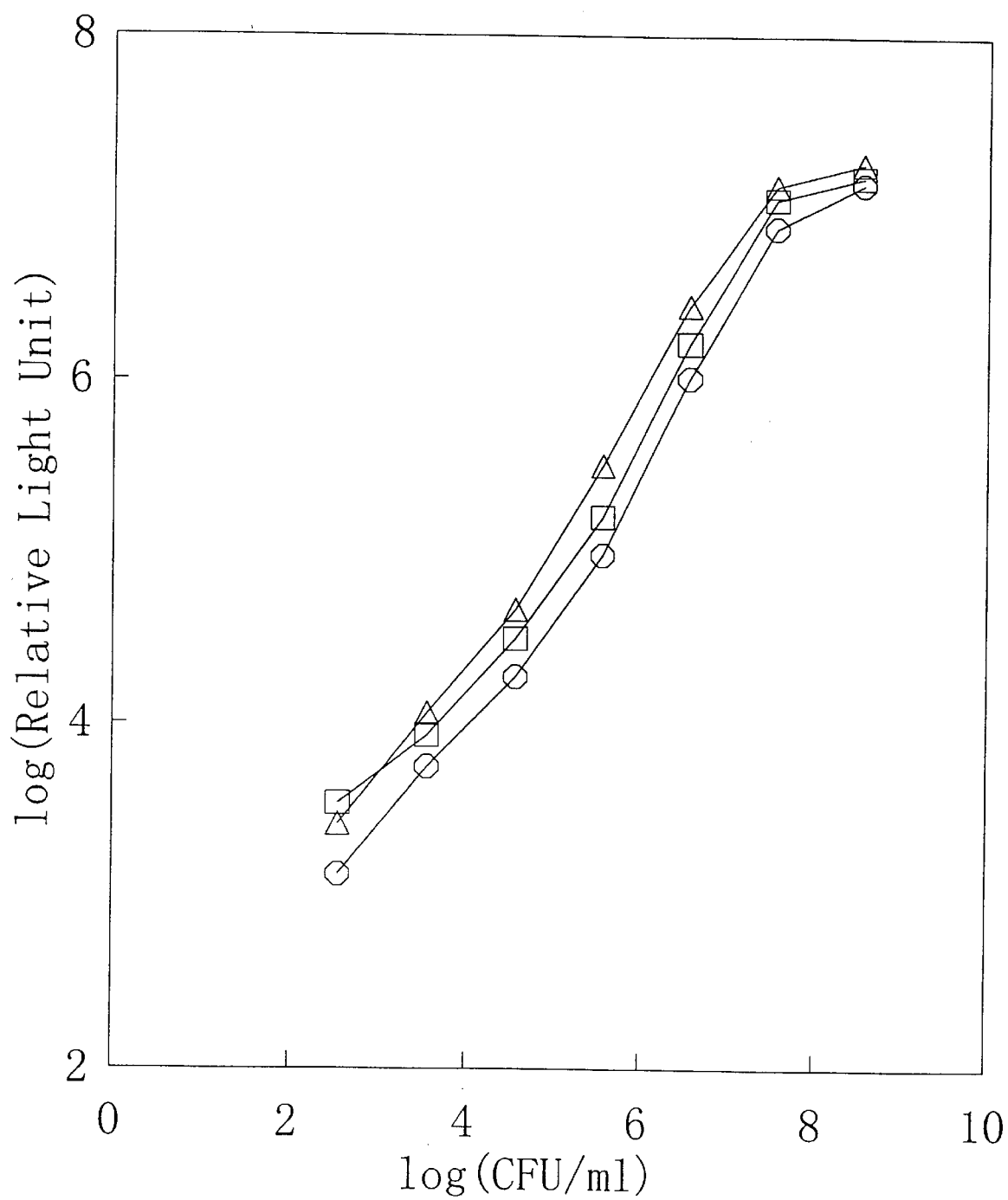
FIG. 9 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that sodium azide or cresol was used instead of penicillin G—Na salt as a preservative at the same concentration in the ATP hydrolase-containing aqueous solution shown in step 7) of Example 1. The results are shown in FIG. 9. In this Figure, ○ represents the results for the case where sodium azide was used; Δ represents the results for the case of cresol; and □ represents the results for sample A in Example 1.

When sodium azide or cresol is used as a preservative, linearity is also observed between the cell number and the relative light unit if the cell number (logCFU) is in the range of from 3 to 8. Also, good correlation is observed with sample A of Example 1. Thus, it is shown that the cell number (logCFU) can be quantitatively determined from the relative light unit when the cell number (logCFU) is in the range of from 3 to 8.

EXAMPLE 6

Figure 10:
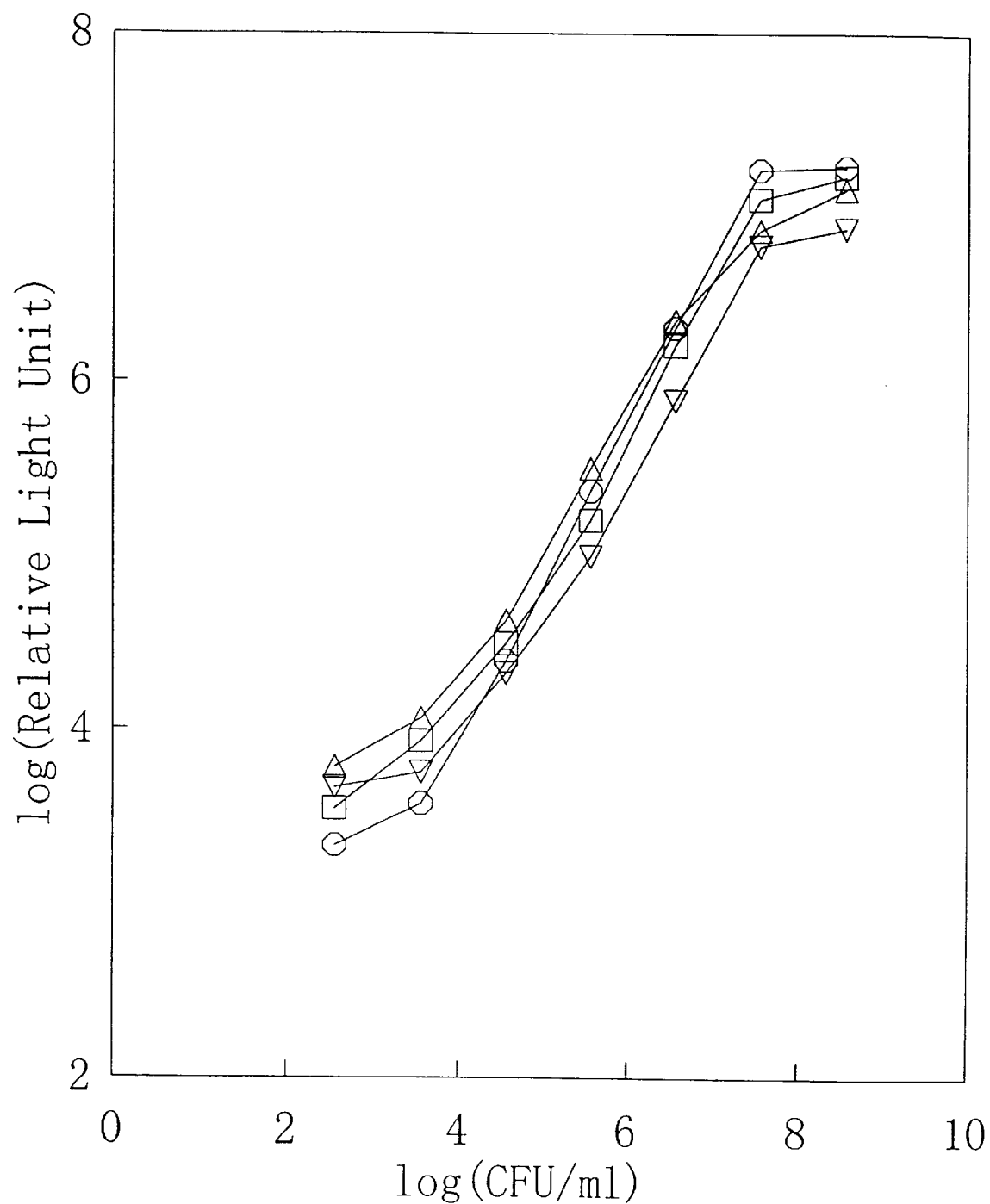
FIG. 10 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that MES-NaOH buffer (pH 6.5), HEPES-NaOH buffer (pH 7.0) or Tris-HCl buffer (pH 7.5) was used instead of MOPS-NaOH buffer (pH 7.0) at the same concentration in the ATP hydrolase-containing aqueous solution shown in step 7) of Example 1. The results are shown in FIG. 10. In this Figure, ○ represents the results when MES-NaOH buffer was used; Δ represents the results for the case where HEPES-NaOH buffer was used; ∇ represents the results for the case of Tris-HCl buffer; and □ represents the results for sample A in Example 1.

When MES-NaOH buffer, HEPES-NaOH buffer or Tris-HCl buffer is used as a buffer, linearity is also observed between the cell number and the relative light unit if the cell number (logCFU) is in the range of from 3 to 8. Also, good correlation is observed with sample A of Example 1. Thus, it is shown that the cell number (logCFU) can be quantitatively determined from the relative light unit when the cell number (logCFU) is in the range of from 3 to 8.

EXAMPLE 7

A test kit comprising Reagent A, Reagent B, Reagent C, a bioluminescence reagent, ATP standard solution and dissolving solutions therefor was prepared as follows.

Preparation of Reagent A: 1.5 M ADA solution (pH 6.8) was prepared as a chelating agent and 10% Triton X-100 solution was prepared as a nonionic surface active agent. For the adjustment of pH in the ADA aqueous solution, 10N NaOH solution was used.

In a 500 ml measuring cylinder, 15 ml of 10% Triton X-100 solution was placed, and sterilized ultrapure water was added to give a 150 ml solution. To this solution, 30 ml of 1.5 M ADA solution was added and dissolved with sufficient agitation. Then, the solution was diluted to give a total volume of 300 ml. The resultant solution was sterilized through a 0.2 μm filter. Then, 300 μl of 10% polystyrene latex (Sekisui Chemical Co., Ltd.; Latex Soap-Free Type N-800; particle size: 0.78 μm) was added aseptically.

The resultant solution was dispensed in 50 ml portions into sterilized 60 ml PETG containers to obtain Reagent A.

Preparation of Reagent B: To 25 mM HEPES buffer (pH 7.0), serum albumin (from bovine; INTERGEN), calcium chloride, magnesium chloride and EDTA were added to give concentrations of 12 mg/ml, 24 mM, 0.6 mM and 1.2 mM, respectively. Then, apyrase (from potato; Sigma; Grade VI) was added to give an enzyme activity (Δ logRLU/min) of 24.

The mixture was sterilized through a 0.45 μm filter, dispensed in 1 ml portions into brown glass bottles for vacuum freeze-drying, freeze-dried at −40° C. for 24 hours, and then vacuum-packed and sealed tightly with a rubber plug. At the time of measurement, this freeze-dried material was dissolved in 12 ml of 25 mM HEPES buffer (pH 7.0) containing 0.1% sodium azide and used as Reagent B.

Preparation of Reagent C: To a 500 ml flask, 197.25 ml of sterilized ultrapure water, 0.75 ml of chlorhexidine digluconate (20% solution; Aldrich) and 2 ml of 0.75% CTAB solution were added and mixed with sufficient agitation. The mixture is sterilized through a 0.2 μm filter, dispensed in 12 ml portions into sterilized 15 ml HDPE shading containers and tightly sealed. Thus, Reagent C was obtained.

Preparation of a bioluminescence reagent: To 150 mM Tris-HCl buffer (pH 7.75), EDTA, magnesium acetate, DTT, serum albumin (from bovine; INTERGEN) and D-luciferin were added to give concentrations of 0.6 mM, 300 mM, 3 mM, 9 mg/ml and 4.5 mM, respectively. To the solution, a purified firefly luciferase was added. At this time, the amount of the luciferase was adjusted so that luminescence of about $2 \times 10^6$ RLU was obtained in the presence of $10^{-12}$ mole ATP when an aliquot of the resultant solution was diluted 6 folds with sterilized ultrapure water.

The resultant solution was sterilized through a 0.45 μm filter, dispensed in 2 ml portions into brown glass bottles for vacuum freeze-drying, freeze-dried at −20° C. for 24 hours, and then vacuum-packed and sealed tightly with a rubber plug.

At the time of measurement, this freeze-dried material was dissolved in 12 ml of ATP-free, sterilized ultrapure water and used as a bioluminescence reagent. Prior to the measurement, the following ATP standard solution was used to confirm that luminescence of almost the same degree as described above could be obtained.

Preparation of ATP standard solution: ATP was dissolved in 10 mM HEPES buffer (pH 7.75) to give a concentration of $2 \times 10^9$ M.

Figure 11:
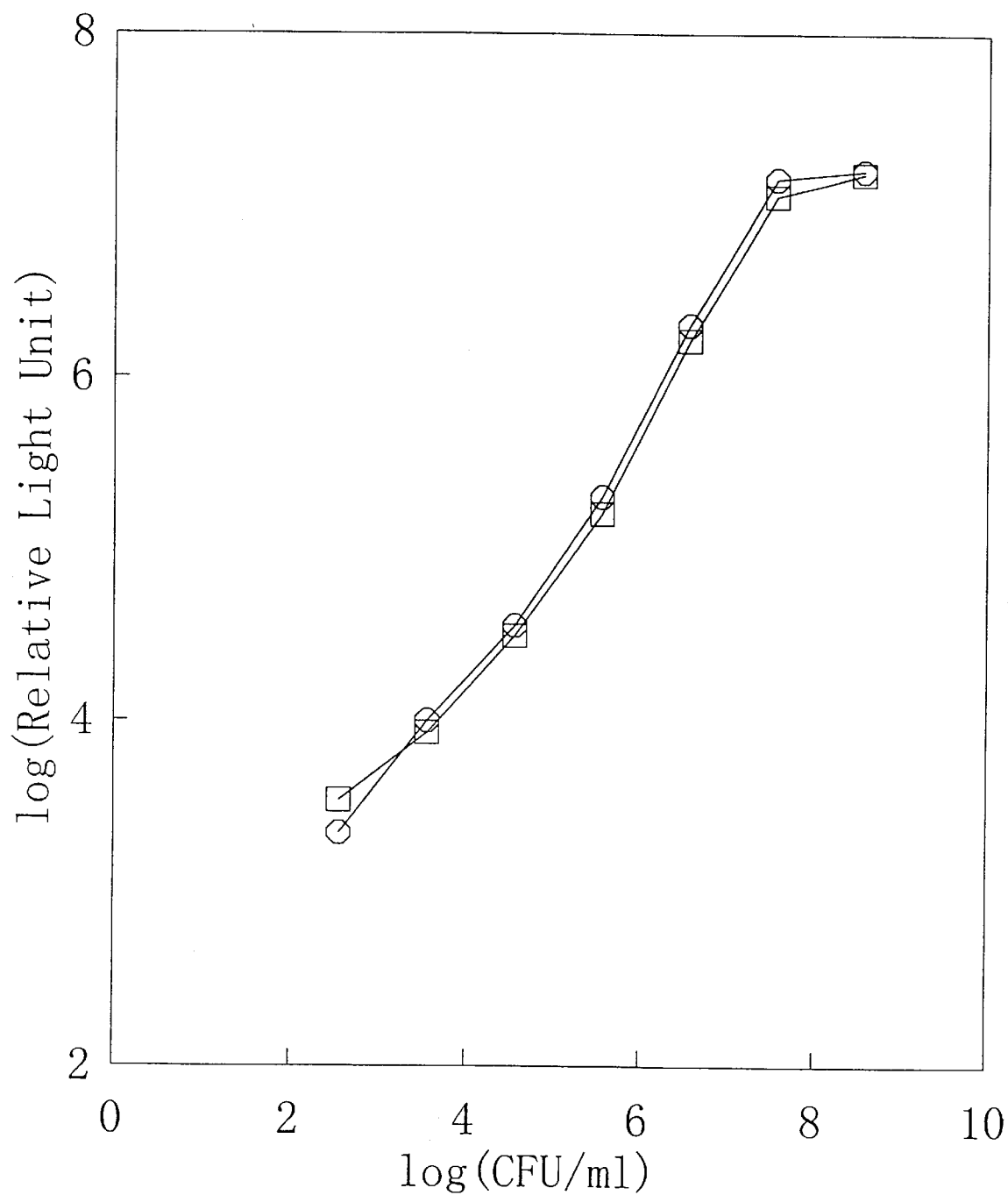
FIG. 11 shows the relation between the cell number (logCFU) and the relative light unit (logRLU) in a sample to which *Staphylococcus aureus* ATCC 6538 has been added.

Using the test kit thus prepared, the relation between the cell number (logCFU) and the relative light unit (logRLU) was examined on sample A in the same manner as described in Example 1. In other words, measurement was performed using Reagent A instead of the "aqueous solution containing a chelating agent and a nonionic surface active agent" in Example 1, Reagent B instead of the "aqueous solution containing ATP hydrolase", Reagent C instead of the "ATP extraction agent", and the bioluminescence reagent instead of the "luminescence agent (Toyo Ink Mfg. Co., Ltd.; product name: Kinshiro)". The results are shown in FIG. 11. In this Figure, ○ represents the results of Example 7 and □ represents the results for sample A in Example 1.

When the above test kit is used, linearity is also observed between the cell number and the relative light unit if the cell number (logCFU) is in the range of from 3 to 8. Also, good correlation is observed with sample A of Example 1. Thus, it is shown that the cell number (logCFU) can be quantitatively determined from the relative light unit when the cell number (logCFU) is in the range of from 3 to 8.

COMPARATIVE EXAMPLE 1

Figure 12:
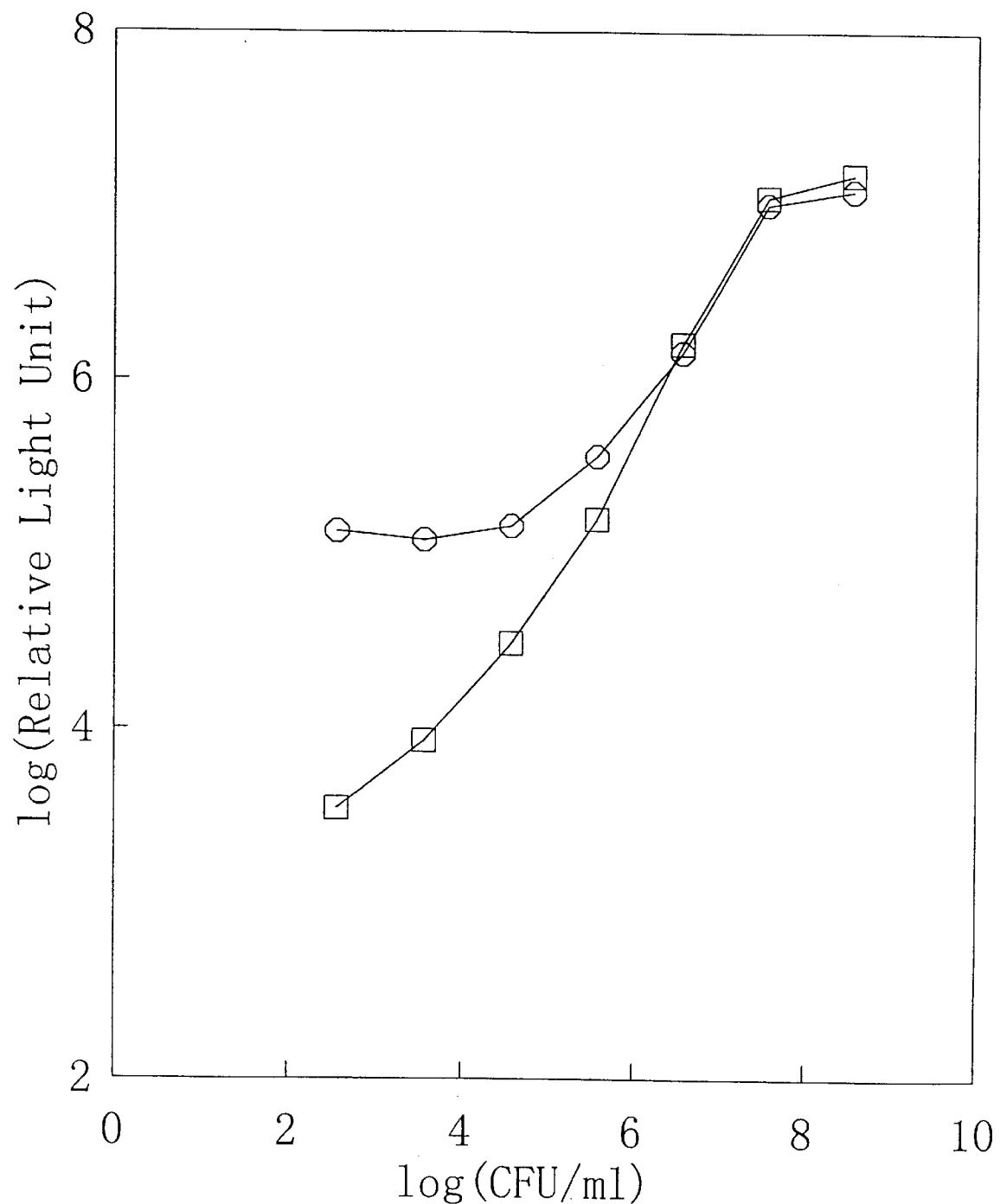
FIG. 12 shows the relation between the cell number (logCFU) and the relative light unit (logRLU) in a sample to which *Staphylococcus aureus* ATCC 6538 has been added.

The following Comparative Examples 1–3 show the results of experiments using *Staphylococcus aureus* ATCC 6538, a representative microorganism which contaminates milk samples The relation between the cell number (logCFU) and the relative light unit (logRLU) was examined on sample A in the same manner as described in Example 1 except that apyrase in the ATP hydrolase-containing aqueous solution shown in step 7) of Example 1 was excluded. The results are shown in FIG. 12. In this Figure, ○ represents the results of Comparative Example 1 and □ represents the results for sample A in Example 1. As shown in this Figure, in the determination method which does not use apyrase, the relative light unit (logRLU) does not decrease if the cell number (logCFU) is 5 or less, nor good correlation is observed with sample A of Example 1. Therefore, this method is inappropriate as a determination method.

COMPARATIVE EXAMPLE 2

Figure 13:
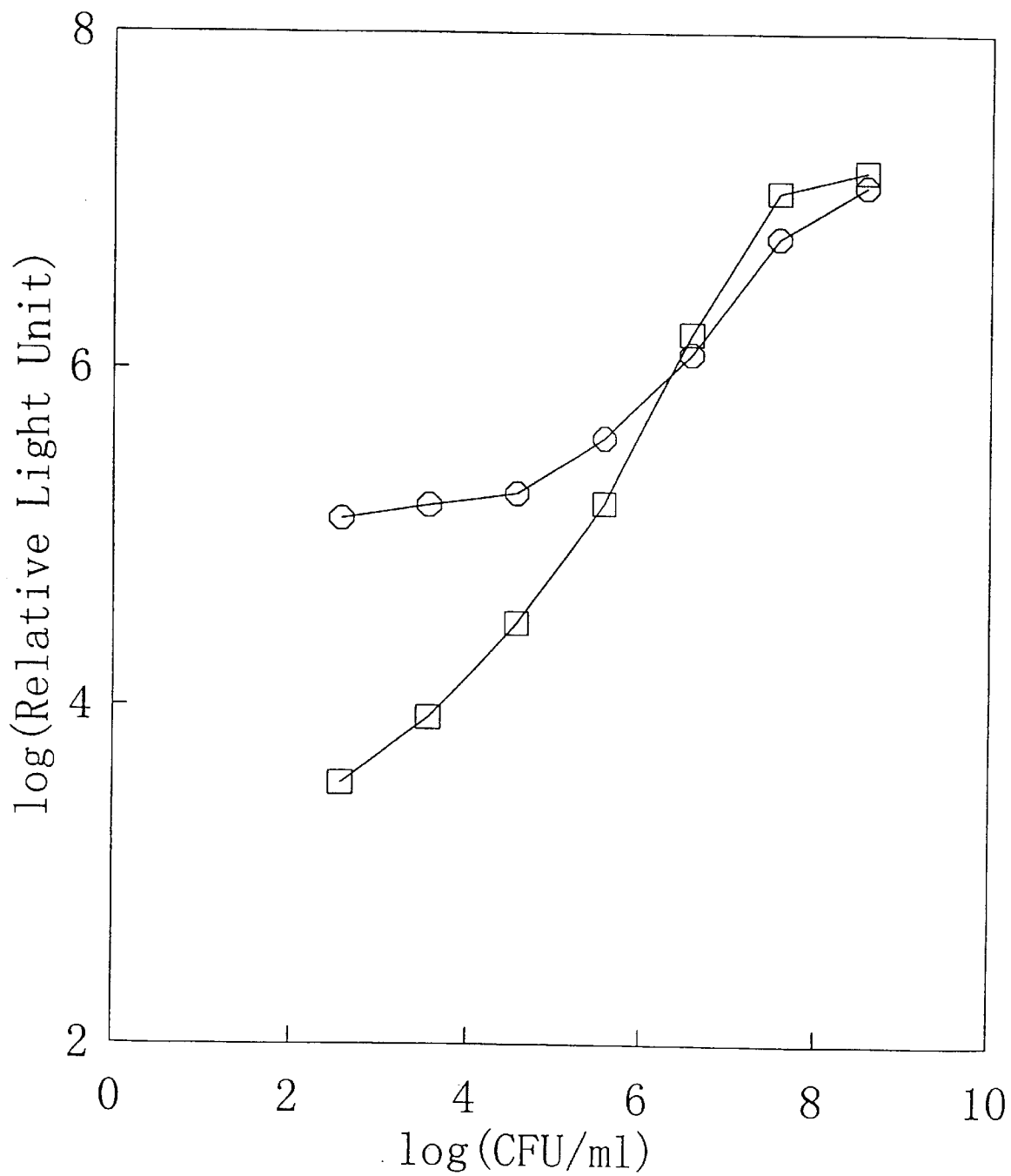
FIG. 13 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that ovalbumin used as a protease-free soluble protein in the ATP hydrolase-containing aqueous solution shown in step 7) of Example 1 was excluded. The results are shown in FIG. 13. In this Figure, ○ represents the results of Comparative Example 2 and □ represents the results for sample A in Example 1. As shown in this Figure, in the determination method which does not use ovalbumin, the relative light unit (logRLU) does not decrease if the cell number (logCFU) is 5 or less, nor good correlation is observed with sample A of Example 1. Therefore, this method is inappropriate as a determination method.

COMPARATIVE EXAMPLE 3

Figure 14:
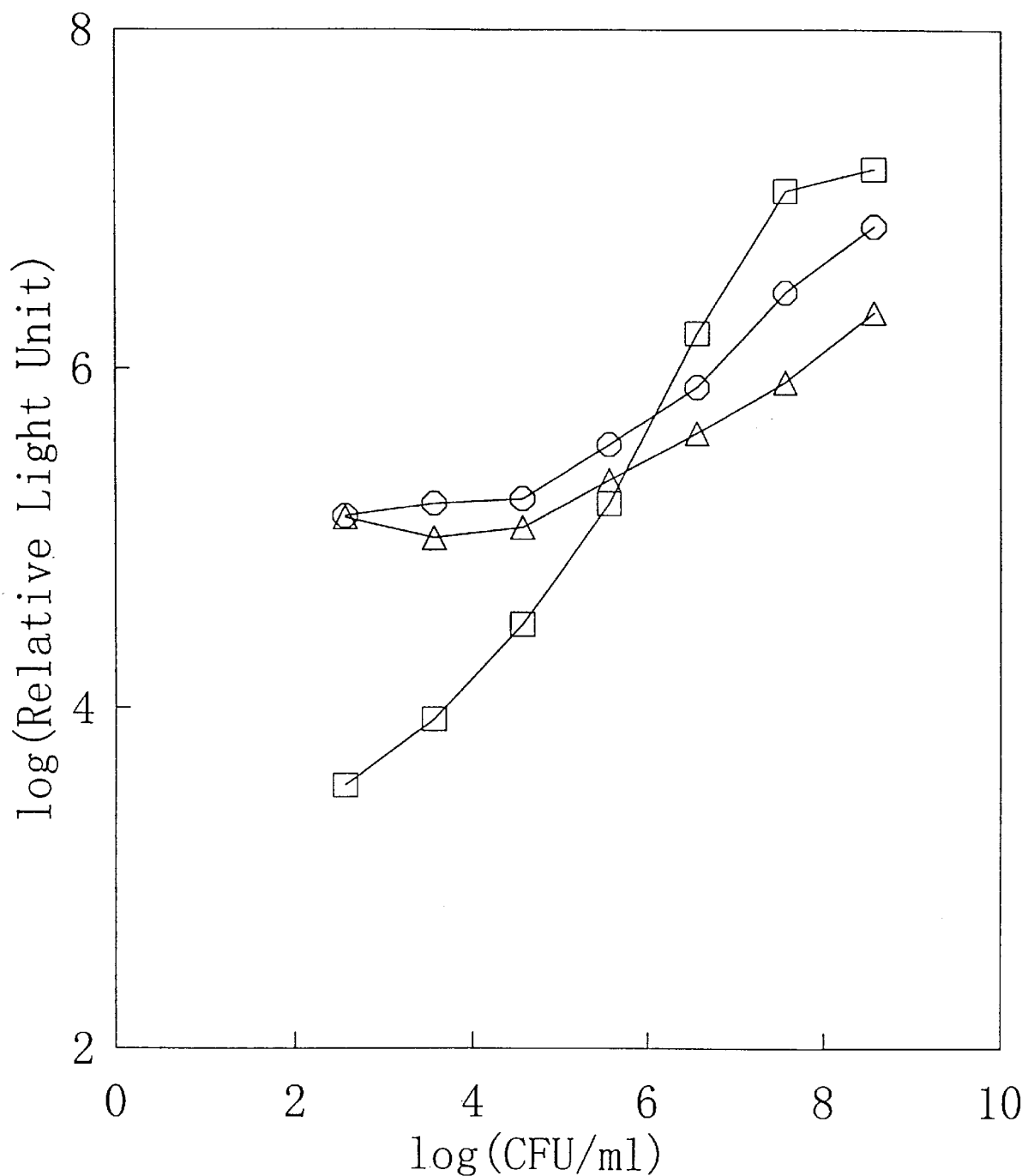
FIG. 14 shows the relation between the cell number (logCFU) and the relative light unit (logRLU) in a sample to which *Staphylococcus aureus* ATCC 6538 has been added.

The relation between the cell number (logCFU) and the relative light unit (logRLU) was examined on sample A in the same manner as described in Example 1 except that sodium succinate buffer (pH 5.0) or GTA buffer (pH 9.0) (described on page 435 in *Basic Experimental Methods on Proteins and Enzymes,* supra) was used instead of MOPS-NaOH buffer (pH 7.0) at the same concentration in the ATP hydrolase-containing aqueous solution shown in step 7) of Example 1. The results are shown in FIG. 14. In this Figure, ○ represents the results for the case where sodium succinate buffer was used; Δ represents the results for the case in GTA buffer; and □ represents the results for sample A in Example 1. As shown in FIG. 14, in the determination methods using a buffer of which the pH region is on the acid or alkali side, the relative light unit (logRLU) does not decrease if the cell number (logCFU) is 5 or less, nor good correlation is observed with sample A of Example 1. Therefore, these methods are inappropriate as a determination method.

According to the present invention, detection sensitivity in a method for selectively detecting and/or determining the ATP from microorganism cells in a sample, particularly, in a milk sample has been greatly improved. By optimizing the activity of an ATP hydrolase in a series of operations consisting of the steps of extracting ATP from non-microorganism cells with a nonionic surface active agent, decomposing the ATP with an ATP hydrolase, then extracting ATP from microorganism cells with an ATP extraction agent and detecting the ATP by bioluminescence analysis, it has become possible to decompose the ATP from non-microorganism cells without damaging the ATP from microorganism cells to thereby minimize the noise due to the ATP from non-microorganism cells. By employing a centrifugal operation jointly, a detection sensitivity of $10^2$–$10^3$ CFU/ml has been achieved for microorganisms in a milk sample. In conventional methods employing a centrifugal operation, it has been necessary to repeat centrifugation in order to completely remove the ATP from non-microorganism cells. In the method of the invention, however, a satisfactory result can be obtained by one centrifugation cycle and, thus, the time for determination can be shortened.

What is claimed is:

1. A method for determining the amount of ATP from microorganism cells in a sample, which comprises the steps of: centrifuging the sample and removing the supernatant, thereby forming a microorganism cell pellet; adding to the microorganism cell pellet a buffer containing a protease-free soluble albumin protein and an ATP hydrolase and incubating the mixture at a pH of 6.0–8.0; extracting ATP from the microorganism cells with an added ATP extraction agent; and determining the amount of ATP released form the microorganism cells by bioluminescence analysis.

2. The method of claim 1, which further includes the step of adding a nonionic surface active agent before centrifugation of the sample such that the ATP in non-microorganism cells in the sample is released to the outside of the cells.

3. The method of claim 2, wherein a chelating agent is added in the step of adding a nonionic surface active agent such that the ATP in non-microorganism cells in the sample is released to the outside of the cells.

4. The method of claim 1, wherein an ATP hydrolase-activating agent is added in the step of adding to the microorganism cell pellet a buffer containing a protease-free soluble albumin protein and an ATP hydrolase and incubating the mixture at a pH of 6.0–8.0.

5. The method of claim 1, wherein an additive selected from the group consisting of antibiotics, azides, phenol compounds and mixtures thereof is added in the step of adding to the microorganism cell pellet a buffer containing a protease-free soluble albumin protein and an ATP hydrolase and incubating the mixture at a pH of 6.0–8.0.

6. The method of claim 1, wherein a chelating agent is added in the step of adding to the microorganism cell pellet a buffer containing a protease-free soluble albumin protein and an ATP hydrolase and incubating the mixture at a pH of 6.0–8.0.

7. The method of claim 1, wherein an agent for protecting —SH groups in proteins is added in the step of adding to the microorganism cell pellet a buffer containing a protease-free soluble albumin protein and an ATP hydrolase and incubating the mixture at a pH of 6.0–8.0.

8. A test kit for determining the amount of ATP from microorganism cells in a sample, which comprises a reagent containing a buffer capable of pH adjustment to 6.0–8.0, a protease-free soluble albumin protein and an ATP hydrolase, a reagent containing an ATP extraction agent, and a bioluminescence reagent.

9. The test kit of claim 8, which further includes a reagent containing a nonionic surface active agent.

10. The test kit of claim 9, wherein the reagent containing a nonionic surface active agent contains a chelating agent.

11. The test kit of claim 8, wherein the reagent containing a buffer capable of pH adjustment to 6.0–8.0, a protease-free soluble albumin protein and an ATP hydrolase contains an ATP hydrolase-activating agent.

12. The test kit of claim 8, wherein the reagent containing a buffer capable of pH adjustment to 6.0–8.0, a protease-free soluble albumin protein and an ATP hydrolase contains an additive selected from the group consisting of antibiotics, azides, phenol compounds and mixtures thereof.

13. The test kit of claim 8, wherein the reagent containing a buffer capable of pH adjustment to 6.0–8.0, a protease-free soluble albumin protein and an ATP hydrolase contains a chelating agent.

14. The test kit of claim 8, wherein the reagent containing a buffer capable of pH adjustment to 6.0–8.0, a protease-free soluble albumin protein and an ATP hydrolase contains an agent for protecting —SH groups in proteins.

15. The test kit of claim 8, wherein the bioluminescence reagent contains luciferin and luciferase.

* * * * *